US011998762B2

(12) United States Patent
Berbeco et al.

(10) Patent No.: US 11,998,762 B2
(45) Date of Patent: Jun. 4, 2024

(54) SYSTEMS AND METHODS FOR TISSUE TRACKING WITH RADIATION THERAPY BEAMS

(71) Applicant: The Brigham and Women's Hospital, Inc., Boston, MA (US)

(72) Inventors: Ross Berbeco, Cohasset, MA (US); Yue-Houng Hu, Rochester, MN (US)

(73) Assignee: The Brigham and Women's Hospital, Inc., Boston, MA (US)

(*) Notice: Subject to any disclaimer, the term of this patent is extended or adjusted under 35 U.S.C. 154(b) by 842 days.

(21) Appl. No.: 17/114,077

(22) Filed: Dec. 7, 2020

(65) Prior Publication Data

US 2021/0170201 A1 Jun. 10, 2021

Related U.S. Application Data

(60) Provisional application No. 62/944,213, filed on Dec. 5, 2019.

(51) Int. Cl.
| | |
|---|---|
| *A61N 5/10* | (2006.01) |
| *A61B 6/42* | (2024.01) |
| *A61B 90/00* | (2016.01) |
| *G01T 1/20* | (2006.01) |
| *G01T 1/202* | (2006.01) |

(52) U.S. Cl.
CPC .......... *A61N 5/1077* (2013.01); *A61B 6/4266* (2013.01); *A61B 90/39* (2016.02); *A61N 5/1045* (2013.01); *A61N 5/1049* (2013.01); *G01T 1/2018* (2013.01); *G01T 1/2023* (2013.01); *A61B 2090/3937* (2016.02)

(58) Field of Classification Search
CPC ...... A61N 5/1077; A61B 90/39; A61B 6/4266
See application file for complete search history.

(56) References Cited

U.S. PATENT DOCUMENTS

| | | | |
|---|---|---|---|
| 9,482,630 B2 | 11/2016 | Wang et al. | |
| 9,545,526 B1 | 1/2017 | Partain | |
| 10,330,798 B2 | 6/2019 | Shedlock et al. | |
| 2010/0316259 A1 | 12/2010 | Liu et al. | |
| 2015/0265851 A1* | 9/2015 | Ma | A61N 5/1037 600/1 |
| 2016/0016009 A1* | 1/2016 | Manzke | A61B 34/20 600/431 |
| 2017/0106213 A1* | 4/2017 | Lee | A61B 6/032 |
| 2018/0333592 A1* | 11/2018 | Fagerstrom | A61N 5/1077 |
| 2018/0336486 A1 | 11/2018 | Chu et al. | |
| 2019/0331808 A1 | 10/2019 | Morf et al. | |
| 2020/0209411 A1* | 7/2020 | Baturin | G01T 1/2008 |
| 2021/0026023 A1* | 1/2021 | Maolinbay | G01T 3/06 |

* cited by examiner

*Primary Examiner* — Hugh Maupin
(74) *Attorney, Agent, or Firm* — Quarles & Brady LLP

(57) ABSTRACT

Some aspects of the disclosure provide a radiation therapy system. The system can include a radiation source configured to emit a radiation therapy beam, a collimator positioned to attenuate at least a periphery of the radiation therapy beam, a radiation fiducial marker configured to be coupled to a patient, and a first radiation detector and a second radiation detector configured to receive the radiation therapy beam after passing through a patient. The system also includes a computer configured to determine a position of the radiation fiducial marker using information from the first detector and the second detector.

24 Claims, 19 Drawing Sheets

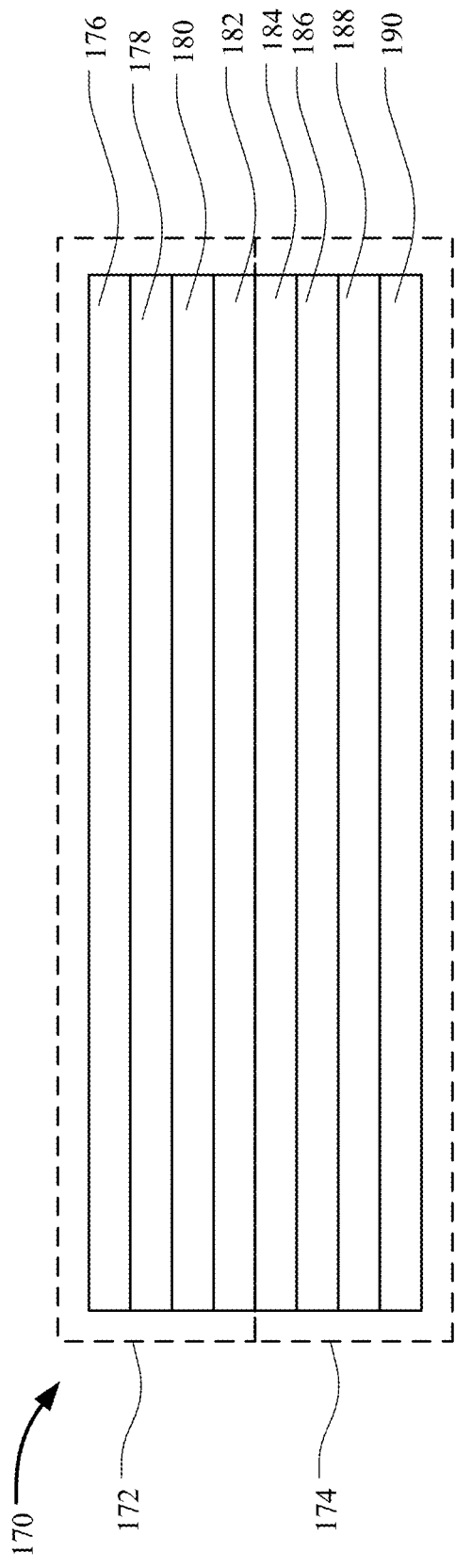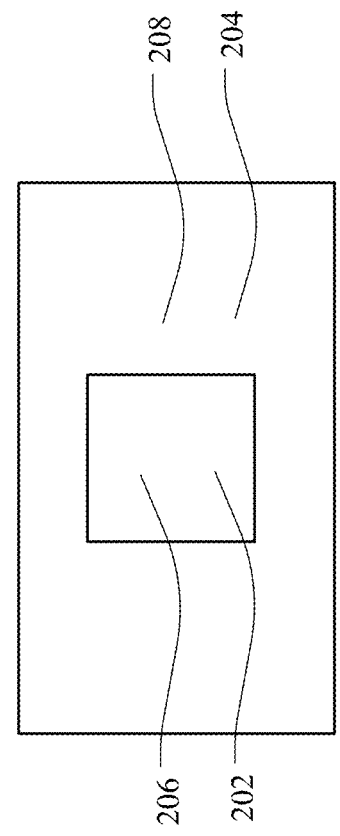
FIG. 3
FIG. 4

SYSTEMS AND METHODS FOR TISSUE TRACKING WITH RADIATION THERAPY BEAMS

CROSS-REFERENCE TO RELATED APPLICATIONS

This application claims priority to U.S. Patent Application No. 62/944,213 filed Dec. 5, 2019, and entitled, "High Dynamic Range Detector for Tumor Tracking with Radiation Therapy Beam," which is hereby incorporated by reference in its entirety.

STATEMENT REGARDING FEDERALLY SPONSORED RESEARCH

This invention was made with government support under R01-CA-188446, awarded by the National Institutes of Health. The government has certain rights in the invention.

BACKGROUND

During external beam radiation therapy, beam's-eye-view ("BEV") imaging of the radiation therapy beam with an electronic portal imaging device ("EPID") may be employed to improve delivery accuracy. For example, tumor tracking has been explored in several contexts, including for both intensity modulated radiation therapy ("IMRT") and volumetric modulated arc therapy ("VMAT"), which may provide better radiation targeting of the tumor. However, in some cases, successfully tracking a tumor using only the BEV can be difficult. Thus, it would be desirable to provide improved tissue tracking with radiation therapy beams.

SUMMARY OF THE DISCLOSURE

Some aspects of the disclosure provide a radiation therapy imaging system for use during a radiation therapy treatment session that can track the position of a radiation fiducial marker coupled to a patient regardless of whether the radiation fiducial marker is located inside or out of the BEV.

Some aspects of the disclosure provide systems and methods for tissue tracking with radiation therapy beams.

Some aspects of the disclosure provide a radiation therapy system. The radiation therapy system can include a radiation source configured to emit a radiation therapy beam, a collimator positioned to attenuate at least a periphery of the radiation therapy beam, a radiation fiducial configured to be coupled to a patient, a first radiation detector having a first plurality of sensing elements each configured to sense radiation that interacts with the respective sensing element, a second radiation detector having a second plurality of sensing elements each configured to sense radiation that interacts with the respective sensing element, wherein the second radiation detector is arranged more distally from the radiation source than the first radiation detector to receive the radiation therapy beam after the first radiation detector, and a computing device in communication with the radiation source, the first radiation detector, and the second radiation detector. The computing device can be configured to receive first imaging data from the first radiation detector, receive second imaging data from the second radiation detector, and track a position of the imaging fiducial based on the first imaging data and the second imaging data.

In some non-limiting examples, when the radiation fiducial is situated outside the periphery of the radiation therapy beam, the computing device is configured to track a position of the radiation imaging fiducial based on the first imaging data and the second imaging data.

In some non-limiting examples, the first radiation detector has a first gain, and the second radiation detector has a second gain. In some non-limiting examples, the second gain of the second radiation detector is greater than the first gain of the first radiation detector.

In some non-limiting examples, the first radiation detector includes a gadolinium oxysulfide (GOS) detector, and the second radiation detector includes a layer of scintillating glass. In some non-limiting examples, the scintillating glass is pixelated. In some non-limiting examples, the scintillating glass is a LKH-5 scintillating glass.

In some non-limiting examples, the computing device can be configured to generate a first image using the first imaging data, generate a second image using the second imaging data, and combine the first image and the second image by weighting the second image over the first image when the fiducial is within the periphery of the radiation therapy beam.

In some non-limiting examples, the computing device can be configured to segment a portion of the second image that corresponds to an envelope of the periphery of the radiation therapy beam, and locate the imaging fiducial in a remaining portion of the second image that does not include the envelope of the periphery of the radiation therapy beam, to determine that the fiducial is within the periphery of the radiation therapy beam.

In some non-limiting examples, the computing device can be further configured to process the remaining portion of the second image by filtering the remaining portion of the second image using a median filter having a width and a length. In some non-limiting examples, a ratio of the length to the width of the median filter is approximately 40.

In some non-limiting examples, the remaining portion of the second image surrounds and encapsulates the envelope of the periphery of the radiation therapy beam to define a circular void.

In some non-limiting examples, the region defined by the portion of the second image that corresponds to the envelope is a predefined region, the size and shape of the predefined region being based on the properties of the radiation beam and a distance the radiation beam traverses along a path from the collimator and to the first radiation detector. In some non-limiting examples, the computing device can be configured to determine a boundary of the envelope of the periphery of the radiation therapy beam from the first image, the boundary of the envelope of the periphery being used to define the portion of the second image that is to be segmented.

In some non-limiting examples, to combine the first image and the second image, the computing device can be configured to subtract the second image from the first image to generate a subtracted second image, and locate the imaging fiducial in the subtracted second image.

In some non-limiting examples, the first plurality of sensing elements defines a first sensing area of the first radiation detector. In some non-limiting examples, the second plurality of sensing elements defines a second sensing area of the second radiation detector. In some non-limiting examples, the first sensing area is substantially aligned with the second sensing area so that the first sensing area substantially overlaps with the second sensing area.

In some non-limiting examples, the first sensing area is substantially similar to the second sensing area. In some non-limiting examples, the size of each of the first plurality of sensing elements is substantially similar to the size of each of the second plurality of sensing elements. In some non-limiting examples, the number of the first plurality of sensing elements is substantially similar to the number of the second plurality of sensing elements.

In some non-limiting examples, the radiation therapy system can include a third radiation detector having a third plurality of sensing elements each configured to sense radiation that interacts with the respective sensing element, a fourth radiation detector having a fourth plurality of sensing elements each configured to sense radiation that interacts with the respective sensing element. The second radiation detector can be situated more proximate to the radiation source than the third radiation detector, and the third radiation detector can be situated more proximate to the radiation source than the fourth radiation detector. In some non-limiting examples, the computing device can be configured to receive third imaging data from the third radiation detector, receive fourth imaging data from the fourth radiation detector, generate a first image from the first imaging data, generate a second image by combining at least two of the second imaging data, the third imaging data, or the fourth imaging data, and locate the imaging fiducial in the second image to track the position of the imaging fiducial.

In some non-limiting examples, generating the second image can include the computing device being configured to combine the second imaging data, the third imaging data, and the fourth imaging data together to generate combined imaging data, and generate the second image using the combined imaging data. In some non-limiting examples, the computing device can be configured to segment a portion of the second image that corresponds to a region within the attenuated periphery of the radiation therapy beam, or subtract the second image from the first image to generate a subtracted second image. In some non-limiting examples, the computing device can be configured to locate the imaging fiducial in the remaining portion of the second image, or the subtracted second image.

In some non-limiting examples, gains of the second, third, and fourth detectors are substantially similar. A gain of the second detector can be greater than a gain of the first detector.

In some non-limiting examples, the first imaging data is first three-dimensional (3D) imaging data, and the second imaging data is second 3D imaging data.

Some aspects of the disclosure provide a method for performing a radiation therapy treatment. The method can include delivering a radiation therapy beam from a radiation source to a patient having a fiducial marker positioned on the patient during a radiation therapy treatment, receiving the radiation therapy beam after passing through the patient using a first radiation detector tuned to acquire first imaging data, attenuating at least a portion of the radiation therapy beam as it travels from the radiation source to the patient, receiving the radiation therapy beam after passing through the patient using a second radiation detector tuned to acquire second imaging data at an attenuated intensity level corresponding to the portion of the radiation therapy beam that is attenuated, receiving, using one or more processors, the first imaging data and the second imaging data, and reconstructing, using the one or more processors, images including the fiducial marker based on the first and second imaging data, when the fiducial marker is irradiated by the at least a portion of the radiation therapy beam that is attenuated.

In some non-limiting examples, the gain of the second radiation detector is greater than the gain of the first radiation detector.

In some non-limiting examples, the method can include combining the first and second imaging data to track a position of the fiducial marker.

Some aspects of the disclosure provide a radiation therapy system. The system can include a radiation source configured to emit a radiation therapy beam toward a patient at a selected intensity level, a collimator positioned to receive the radiation therapy beam before reaching the patient and to attenuate at least a periphery of the radiation therapy beam to an attenuated intensity level, a radiation fiducial configured to be coupled to a patient, a first radiation detector positioned to acquire first imaging data from the patient using a first plurality of sensing elements tuned to acquire the radiation therapy beam at the selected intensity level, a second radiation detector positioned to acquire second imaging data from the patient using a second plurality of sensing elements tuned to acquire the radiation therapy beam at the attenuated intensity level, and a processor configured to receive the first imaging data and the second imaging data and selective combine the first imaging data and the second imaging data to track the position of the imaging fiducial.

In some non-limiting examples, the gain of the second radiation detector is greater than the gain of the first radiation detector.

Some aspects of the disclosure provide a radiation therapy system. The system can include a collimator, a radiation source configured to emit a first radiation therapy beam through the collimator, the first radiation therapy beam being restricted by the collimator from the first radiation therapy beam having a first width to a second radiation therapy beam having a second width smaller than the first width, a radiation fiducial marker configured to be coupled to a patient, a first radiation detector having a first plurality of sensing elements each configured to sense radiation that interacts with the respective sensing element, the first radiation detector configured to acquire first imaging data, and a second radiation detector having a second plurality of sensing elements each configured to sense radiation that interacts with the respective sensing element, the first radiation detector being situated above the second radiation detector so that radiation from the radiation source interacts with the first radiation detector before the second radiation detector, the second radiation detector configured to acquire second imaging data. The second imaging data and not the first imaging data can be used to track the position of the radiation fiducial marker. A gain of the second radiation detector can be greater than a gain of the first radiation detector.

In some non-limiting examples, a surface of the first radiation detector and a surface of the second radiation detector are co-planar.

In some non-limiting examples, the perimeter of the second radiation detector is located within the perimeter of the first radiation detector.

In some non-limiting examples, the first radiation detector is coaxial with the second radiation detector.

Some aspects of the disclosure provide a radiation therapy system. The system can include an adjustable collimator, a radiation source configured to emit a first radiation therapy beam through the adjustable collimator, the first radiation therapy beam being restricted by the adjustable collimator from the first radiation therapy beam having a first width to a second radiation therapy beam having a second width smaller than the first width, a radiation fiducial marker configured to be coupled to a patient, a first radiation detector having a first plurality of sensing elements each configured to sense radiation that interacts with the respective sensing element, and a second radiation detector having a second plurality of sensing elements each configured to sense radiation that interacts with the respective sensing element, the first radiation detector being situated above the second radiation detector so that radiation from the radiation source interacts with the first radiation detector before the second radiation detector, the first radiation detector being coaxial with the second radiation detector. A gain of the second radiation detector can be greater than a gain of the first radiation detector. When the radiation fiducial marker is situated in the second radiation therapy beam, the first radiation detector can be configured to sense the position of the radiation fiducial marker. When the radiation fiducial marker is situated in the first radiation therapy beam and not in the second radiation therapy beam, the second radiation detector can be configured to sense the position of the radiation fiducial marker.

Some aspects of the disclosure provide a computer-implemented method for tracking a radiation fiducial marker during a radiation therapy treatment. The method can include causing, using one or more computing devices, a radiation source to emit a radiation therapy beam through a collimator and to a patient, the radiation therapy beam having a first profile that is attenuated to a second profile that is smaller than the first profile, as the radiation therapy beam is passed through the collimator, the first profile and the second profile being coaxial, receiving, using the one or more computing devices, first imaging data from a first radiation detector that includes a first plurality of sensing elements, the first radiation detector interacting with the radiation therapy beam, receiving, using the one or more computing devices, second imaging data from a second radiation detector that includes a second plurality of sensing elements, the second radiation detector interacting with the radiation therapy beam, and tracking, using the one or more computing devices, the location of the radiation fiducial marker when a portion of the radiation fiducial marker is positioned within the first profile of the radiation therapy beam and is not positioned within the second profile of the attenuated radiation therapy beam using the second imaging data.

In some non-limiting examples, a gain of the second radiation detector is greater than a gain of the first radiation detector.

In some non-limiting examples, the method can include generating, using the one or more computing devices, a first image using the first imaging data, generating, using the one or more computing devices, a second image using the second imaging data, and segmenting and removing, using the one or more computing devices, a portion of the second image that corresponds to an envelope of the attenuated radiation therapy beam.

In some non-limiting examples, the method can include processing, using the one or more computing devices, the remaining portion of the second image by filtering, using the one or more computing devices, the remaining portion of the second image using a median filter having a length and a width. A ratio between the length and the width of the median filter can be 40.

In some non-limiting examples, a remaining portion of the second image surrounds and encapsulates a void defined by the segmented portion of the second image. The segmented portion can be circular in shape.

In some non-limiting examples, a perimeter of the void defined by the segmented portion of the second image is a predefined perimeter, the size and shape of the predefined perimeter being based on the properties of the attenuated radiation therapy beam and a distance the attenuated radiation therapy beam traverses along a path from the collimator and to the first radiation detector.

In some non-limiting examples, the method can include determining, using one or more computing devices, a boundary of the envelope of the attenuated radiation therapy beam from the first image; and segmenting and removing, using the one or more computing devices, the portion of the second image based on the size and shape of the boundary.

In some non-limiting examples, the method can include generating, using the one or more computing devices, a first image using the first imaging data, and generating, using the one or more computing devices, a second image using the second imaging data, subtracting, using the one or more computing devices, the second image from the first image to generate a subtracted second image, and locating, using the one or more computing devices, the radiation fiducial marker in the subtracted second image to track the location of the radiation fiducial marker when the portion of the radiation fiducial marker is positioned within the first profile of the radiation therapy beam and is not positioned within the second profile of the attenuated radiation therapy beam.

In some non-limiting examples, the method can include tracking, using the one or more computing devices, the position of the radiation fiducial marker when a second portion of the radiation fiducial marker is positioned within the attenuated radiation therapy beam.

In some non-limiting examples, the method can include receiving, using the one or more computing devices, third imaging data from a third radiation detector having a third plurality of sensing elements, the third radiation detector interacting with the radiation therapy beam, combining, using the one or more computing devices, the second imaging data and the third imaging data, and generating, using the one or more computing devices, an image from the combined imaging data to track the location of the radiation fiducial marker when the portion of the radiation fiducial marker is positioned within the first profile of the radiation therapy beam and is not positioned within the second profile of the attenuated radiation therapy beam.

In some non-limiting examples, combining the second imaging data and the third imaging data includes adding, using the one or more computing devices, the second imaging data to the third imaging data. The first plurality of sensing elements defines a first sensing area of the first radiation detector. The second plurality of sensing elements defines a second sensing area of the second radiation detector. The third plurality of sensing elements defines a third sensing area of the second radiation detector. The first sensing area can be substantially aligned with the second sensing area so that the first sensing area substantially overlaps with the second sensing area. The second sensing area can be substantially similar to the second sensing area. The size of each of the first plurality of sensing elements can be substantially similar to the size of each of the second plurality of sensing elements. The number of the first plurality of sensing elements can be substantially similar to the number of the second plurality of sensing elements. Each corresponding region of the first imaging data and the second imaging data can be added together.

In some non-limiting examples, a gain of the third radiation detector is substantially similar to a gain of the second radiation detector. The second radiation detector can be situated above the third radiation detector.

Some aspects of the disclosure provide a computer-implemented method for evaluating an effectiveness of tracking a radiation fiducial marker for a radiation therapy system. The method can include receiving, using one or more computing devices, a template image of the radiation fiducial marker, receiving, using the one or more computing devices, first imaging data from a radiation detector when the radiation fiducial marker is located within a first radiation therapy beam and not a second radiation therapy beam, the first radiation therapy beam being emitted through a collimator to generate the second radiation therapy beam, the first and second radiation therapy beams being coaxial, generating, using the one or more computing devices, a first image using the first imaging data, determining, using the one or more computing devices, a cross-correlation between the template image and the first image, and determining, using the one or more computing devices, a peak to sidelobe ratio using the cross-correlation. The method can include determining, using the one or more computing devices, that the radiation fiducial marker within the first image is visible, based on the peak to sidelobe ratio. The method can include determining, using the one or more computing devices, the effectiveness of tracking the radiation fiducial marker, based on the peak to sidelobe ratio.

In some non-limiting examples, the dimensions and number of the pixels of the template image and the first image can be substantially similar. The method can include determining, using the one or more computing devices, that the radiation fiducial marker within the first image is visible, based on the peak to sidelobe ratio exceeding a threshold value. The threshold value can correspond to the number of pixels and the dimensions of the template image and the first image.

In some non-limiting examples, the method can include determining, using the one or more computing devices, that the radiation fiducial marker within the first image is visible, based on the peak to sidelobe ratio being greater than or equal to 3.

In some non-limiting examples, the method can include determining, using the one or more computing devices, that the radiation fiducial marker within the first image is visible, based on the peak to sidelobe ratio being greater than or equal to 5.

In some non-limiting examples, the first image defines a corresponding region of interest of 9 square centimeters. The template image can define a corresponding region of interest of 9 square centimeters.

In some non-limiting examples, the template image and the first image have been filtered by using a median filter.

In some non-limiting examples, the first image has been cropped from another image.

In some non-limiting examples, the method can include determining, using the one or more computing devices, an optimal radiation dose for the radiation detector.

In some non-limiting examples, determining the optimal radiation dose for the radiation detector can include acquiring, using the one or more computing devices, a plurality of images from the radiation detector that each correspond to a respective radiation therapy beam, each respective radiation therapy beam being passed through a collimator to generate a respective attenuated radiation therapy beam, each of the plurality of images being acquired when the radiation fiducial marker is located within the respective radiation therapy beam and not the respective attenuated radiation therapy beam, and each respective radiation therapy beam having a different radiation dose, determining, using the one or more computing devices, a plurality of cross-correlations for each pair of the template image and one of the plurality of images for all the pairs, determining, using the one or more computing devices, for each pair, a peak to sidelobe ratio using the respective cross-correlation; determining, using the one or more computing devices, the pair having the highest peak to sidelobe ratio, and determining, using the one or more computing devices, the optimal radiation dose for the radiation detector, based on the pair having the highest peak to sidelobe ratio.

In some non-limiting examples, the optimal radiation dose is a range of monitor units (MUs).

In some non-limiting examples, the radiation fiducial marker is coupled to an object.

In some non-limiting examples, no flattening filter has been applied to the first radiation therapy beam, or the second radiation therapy beam.

Some aspects of the disclosure provide an imaging system for a radiation therapy system having a collimator. The radiation therapy system can be configured to emit a radiation therapy beam through the collimator to define an attenuated radiation therapy beam having a field of view (FOV). The imaging system can include a radiation fiducial marker configured to be coupled to a patient, a first radiation detector having a first plurality of sensing elements each configured to sense radiation that interacts with the respective sensing element, and a second radiation detector having a second plurality of sensing elements each configured to sense radiation that interacts with the respective sensing element, the first radiation detector being situated above the second radiation detector so that radiation from the radiation source interacts with the first radiation detector before the second radiation detector. The first radiation detector and the second radiation detector can be configured to track the location of the radiation fiducial marker regardless of whether the radiation fiducial marker is located within the attenuated radiation therapy FOV, or the radiation therapy beam.

Some aspects of the disclosure provide an imaging system for a radiation therapy system having an adjustable collimator, the radiation therapy system can be configured to emit a radiation therapy beam through the adjustable collimator to define an attenuated radiation therapy beam having a field of view (FOV). The imaging system can include a radiation fiducial marker configured to be coupled to a patient, a first radiation detector having a first plurality of sensing elements each configured to sense radiation that interacts with the respective sensing element, the first radiation detector being configured to track the location of the radiation fiducial marker when the radiation fiducial marker is located within the attenuated radiation therapy beam, and a second radiation detector having a second plurality of sensing elements each configured to sense radiation that interacts with the respective sensing element, the second radiation detector being configured to track the location of the radiation fiducial marker when the radiation fiducial marker is located within the radiation therapy beam and not the attenuated radiation therapy beam. The first radiation detector can be situated above the second radiation detector so that radiation from the radiation source interacts with the first radiation detector before the second radiation detector.

In some non-limiting examples, the location of the radiation fiducial marker can be determined using the first radiation detector and the second radiation detector regardless of whether or not the radiation fiducial marker is located within the attenuated radiation therapy beam.

Some aspects of the disclosure provide a radiation therapy system having a collimator, the radiation therapy system can be configured to emit a radiation therapy beam through the collimator to define an attenuated radiation therapy beam having a field of view (FOV). The system can include a radiation fiducial marker configured to be coupled to a patient, a first radiation detector having a first plurality of sensing elements each configured to sense radiation that interacts with the respective sensing element, the first radiation detector configured to sense the location of the radiation fiducial marker when the radiation fiducial marker is located within the FOV of the attenuated radiation therapy beam, and a second radiation detector having a second plurality of sensing elements each configured to sense radiation that interacts with the respective sensing element, the second radiation detector being configured to sense the location of the radiation fiducial marker when the radiation fiducial marker is not located within the FOV of the attenuated radiation therapy beam. The first radiation detector and the second radiation detector can be configured to track the location of the radiation fiducial marker regardless of whether or not the radiation fiducial marker is located within the attenuated radiation therapy FOV.

Some aspects of the disclosure provide an imaging system for a radiation therapy system having a collimator, the radiation therapy system can be configured to emit a radiation therapy beam through the collimator to define an attenuated radiation therapy beam having a field of view (FOV). The imaging system can include a radiation fiducial marker configured to be coupled to a patient, a first radiation detector having a first plurality of sensing elements each configured to sense radiation that interacts with the respective sensing element, the first radiation detector configured to sense the location of the radiation fiducial marker when the radiation fiducial marker is located within the FOV of the attenuated radiation therapy beam, and a second radiation detector having a second plurality of sensing elements each configured to sense radiation that interacts with the respective sensing element, the second radiation detector being configured to sense the location of the radiation fiducial marker when the radiation fiducial marker is not located within the FOV of the attenuated radiation therapy beam. The first radiation detector and the second radiation detector can be configured to track the location of the radiation fiducial marker regardless of whether or not the radiation fiducial marker is located behind one or more leaves of the collimator.

Some aspects of the disclosure provide a radiation therapy system. The system can include a radiation source configured to emit a radiation therapy beam, a collimator positioned to attenuate at least a periphery of the radiation therapy beam; a radiation fiducial marker configured to be coupled to a patient, a radiation detector having a first plurality of sensing elements each configured to sense radiation that interacts with the respective sensing element, and a computing device in communication with the radiation detector. The computing device can be configured to receive imaging data from the radiation detector, and when the radiation fiducial marker is positioned behind one or more leaves of the collimator, track a position of the radiation fiducial marker.

In some non-limiting examples, the computing device can be configured to move the radiation source to realign the radiation therapy beam with a portion of the patient that includes the radiation fiducial marker, or cause the radiation source to stop emitting the radiation therapy beam, based on the computing device determining that the radiation fiducial marker is behind the one or more leaves of the collimator.

Some aspects of the disclosure provide a radiation therapy system. The system can include a radiation source configured to emit a radiation therapy beam, a collimator positioned to attenuate at least a periphery of the radiation therapy beam, a radiation fiducial marker configured to be coupled to a patient, and a radiation detector having a first plurality of sensing elements each configured to sense radiation that interacts with the respective sensing element, the radiation detector being configured to determine a position of the radiation fiducial marker based on radiation leakage through one or more leaves of the collimator by the radiation therapy beam.

The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTIONS OF THE DRAWINGS

FIG. 3 shows an illustration of a side view of a radiation therapy imaging system.

FIG. 4 shows an illustration of a top view of a radiation therapy imaging system.

Figure 7:
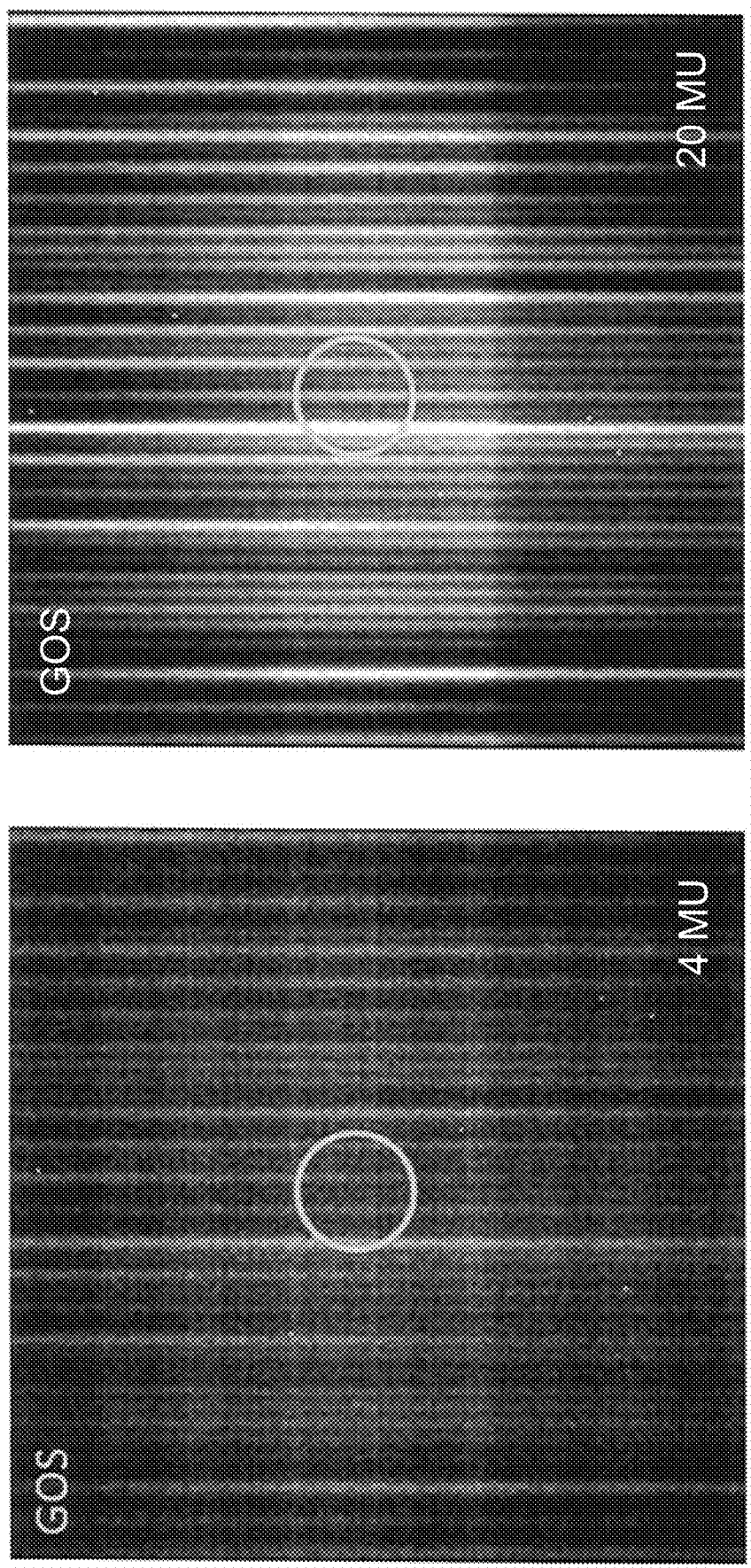

FIG. 7 shows two phantom images acquired at a beam energy of 6×FFF at doses of 4 MU (left) and 20 MU (right) using the GOS detector. The MLC jaws were closed and set to 8×8 cm. The circle indicates the position of the fiducial marker on the image.

Figure 8:
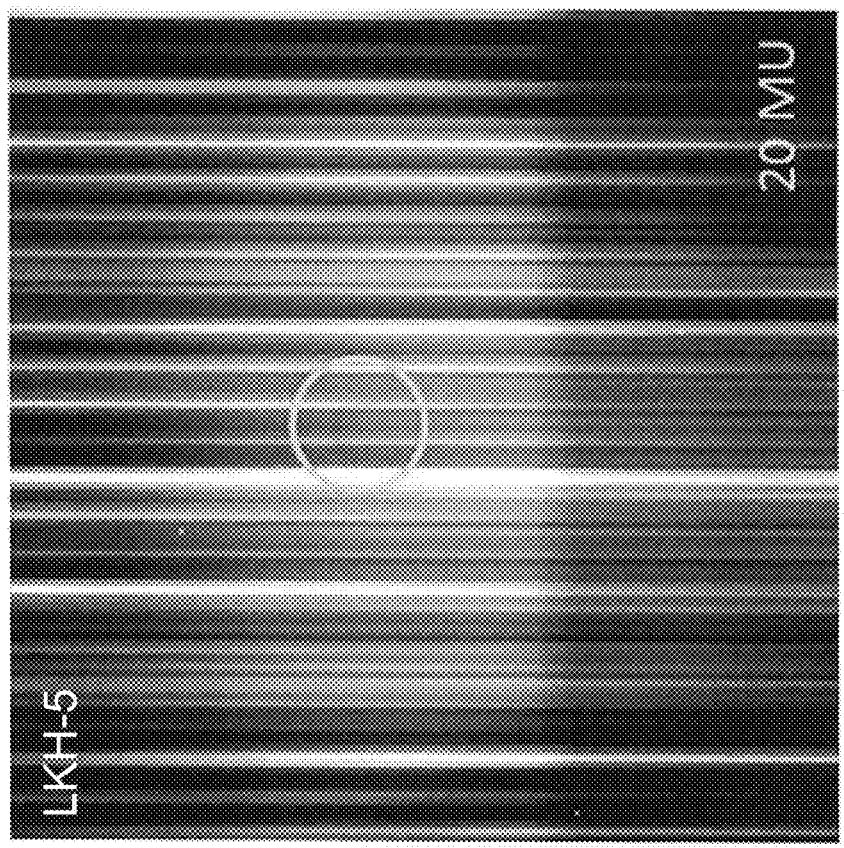
Figure 8:
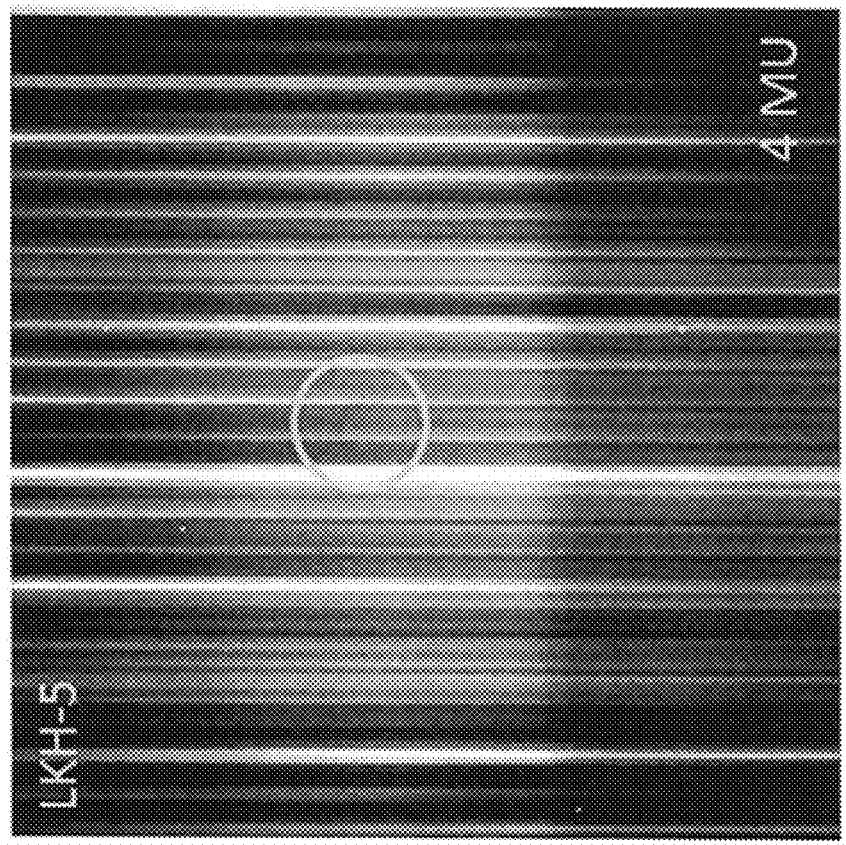

FIG. 8 shows two phantom images acquired at a beam energy of 6×FFF at doses of 4 MU (left) and 20 MU (right) using the LKH-5 detector. The MLC jaws were closed and set to 8×8 cm. The circle indicates the position of the fiducial marker on the image.

Figure 9:
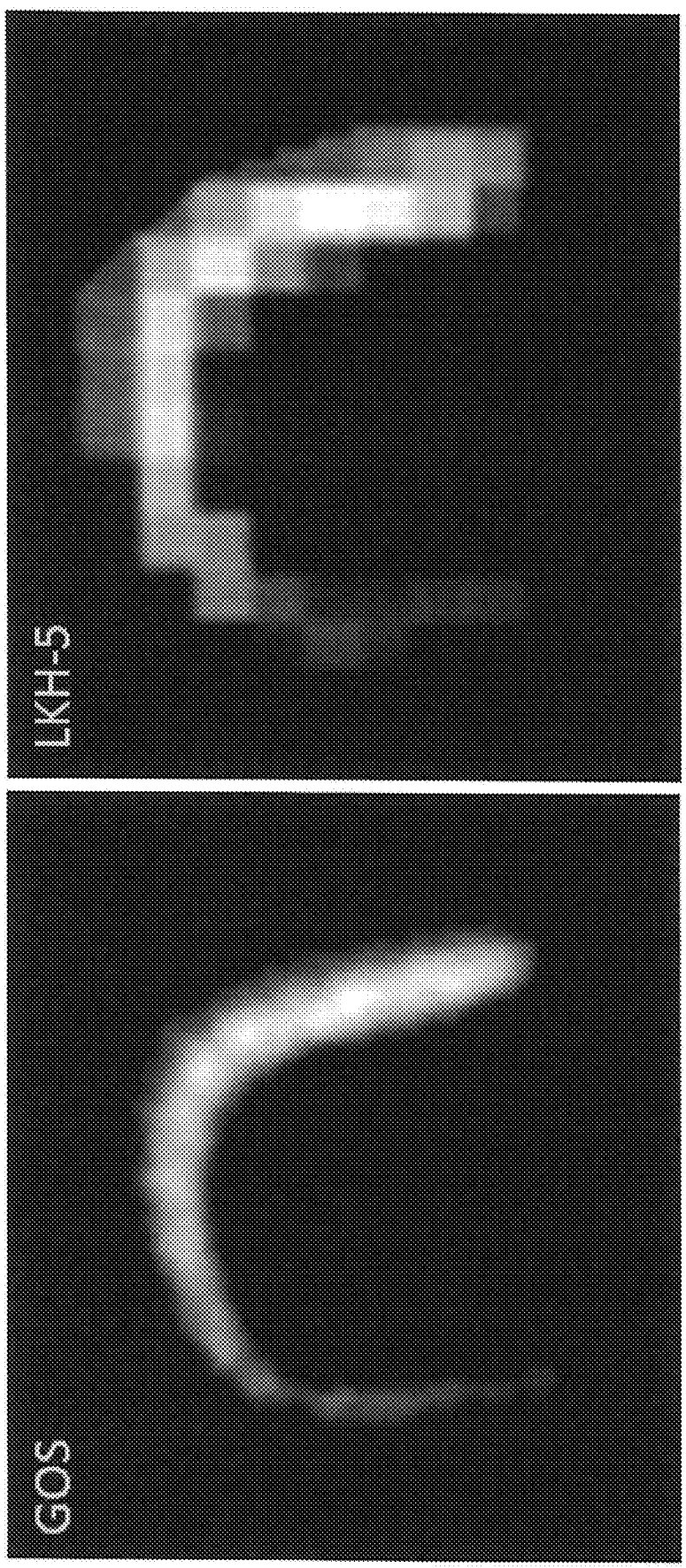

FIG. 9 shows two open-MLC images of the 6×FFF fiducial marker template used for the normalized cross correlation (NCC) with the blocked-MLC (bMLC) images. Images presented as negatives for purposes of visualization.

Figure 10:
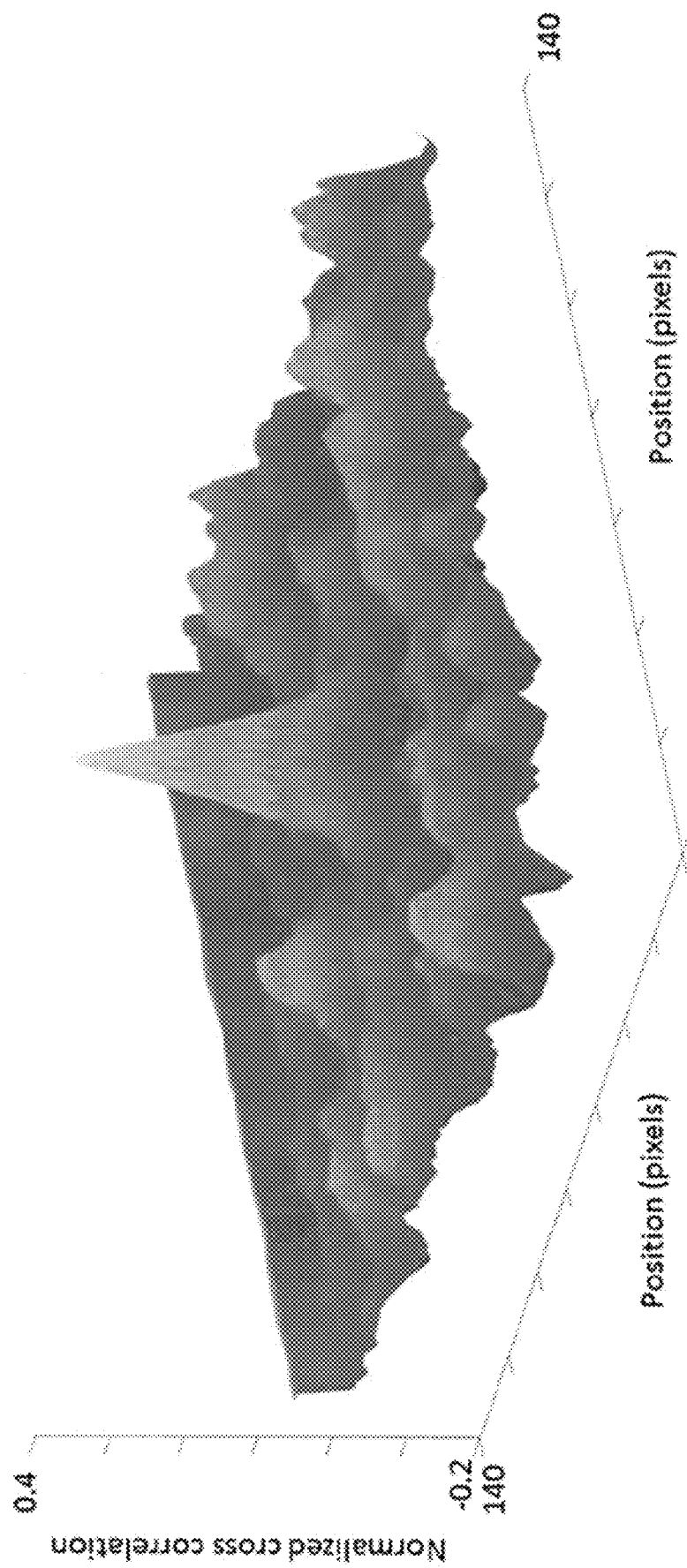

FIG. 10 shows a surface plot of a 133×133 pixel ROI of the NCC of a 4 MU 6×FFF blocked acquisition using the LKH-5 detector. The ROI was centered at the location of the fiducial marker.

Figure 11:
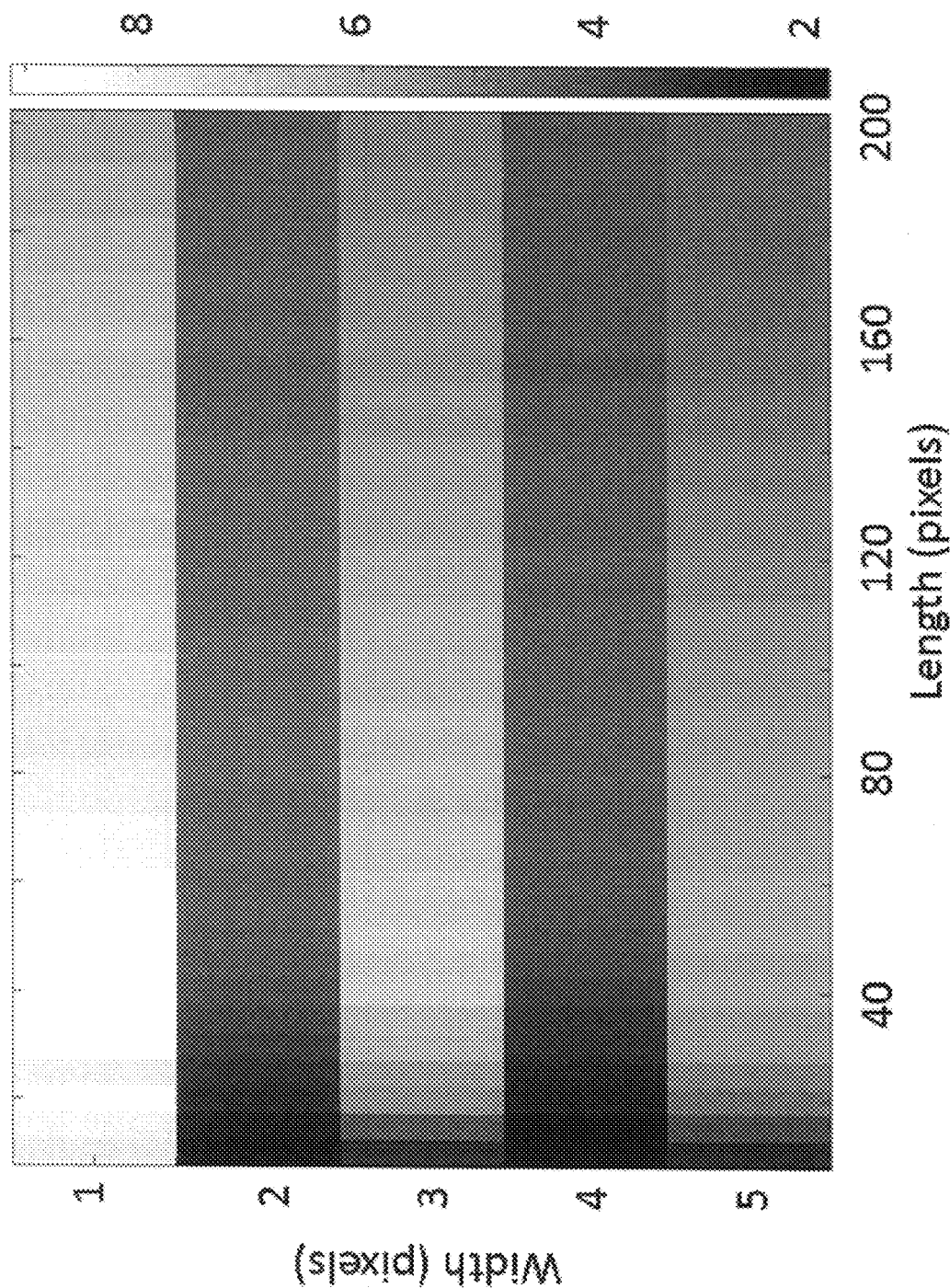

FIG. 11 shows an intensity map indicating the PSR for several median filter sizes. The gray-scale indicates PSR value.

Figure 12:
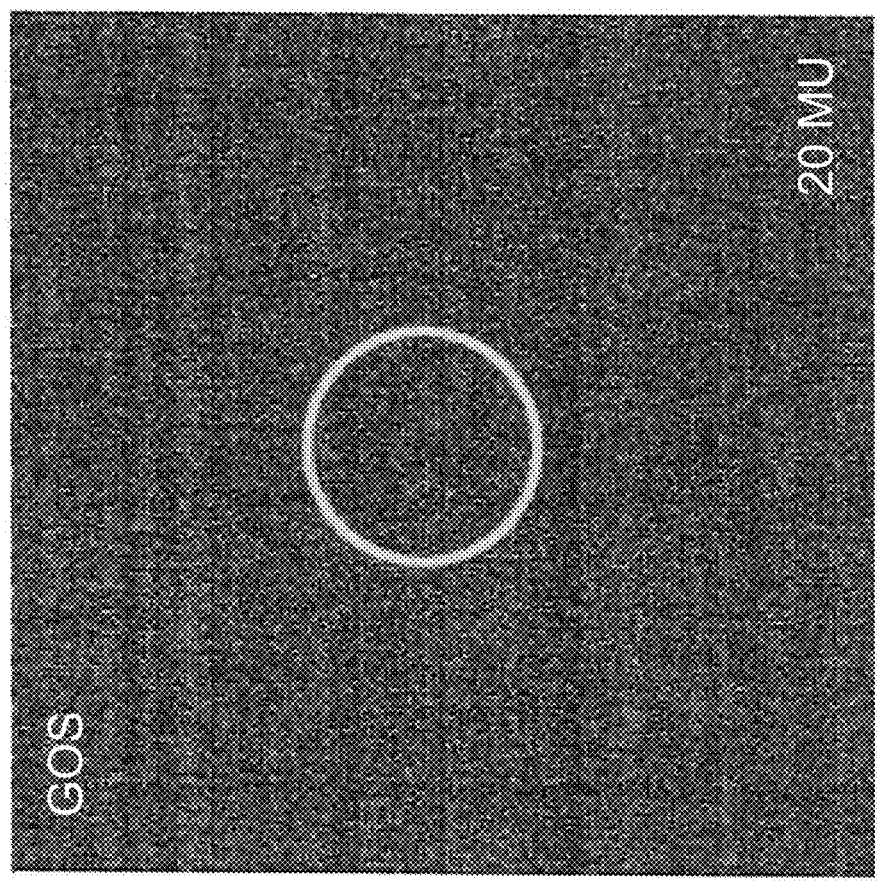
Figure 12:
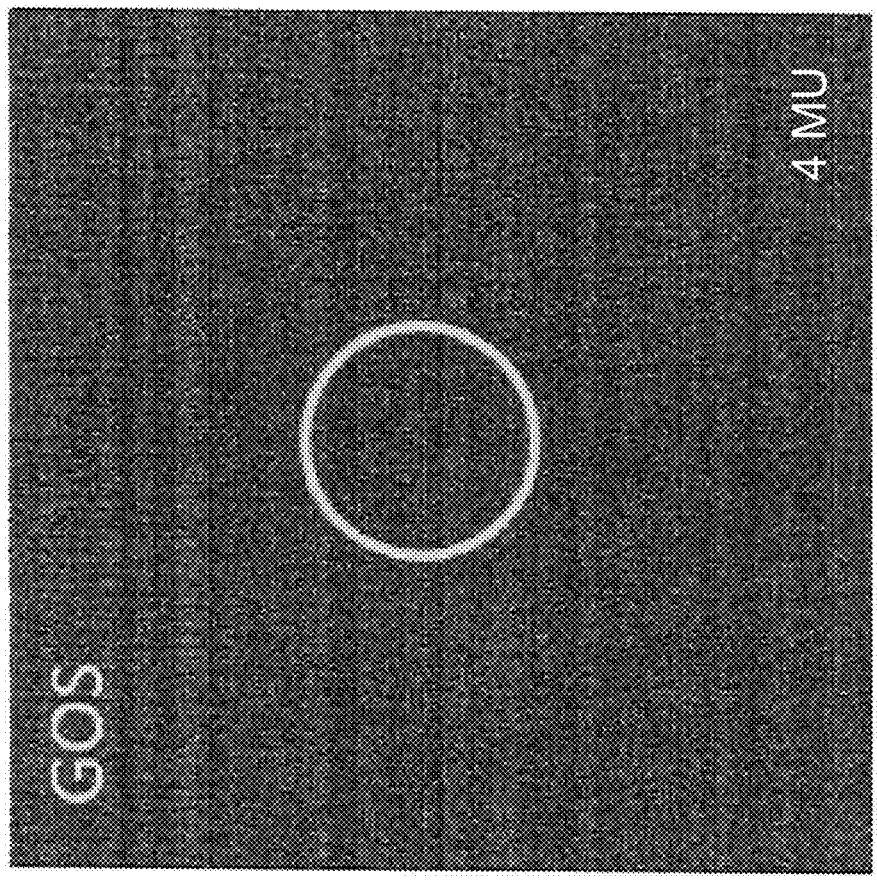

FIG. 12 shows two median filter corrected images for 4 MU (left) and 20 MU (right) 6×FFF exposures using the GOS detector. The median filter size was defined as that which produced the maximum PSR in FIG. 12 (1×40 pixels).

Figure 13:
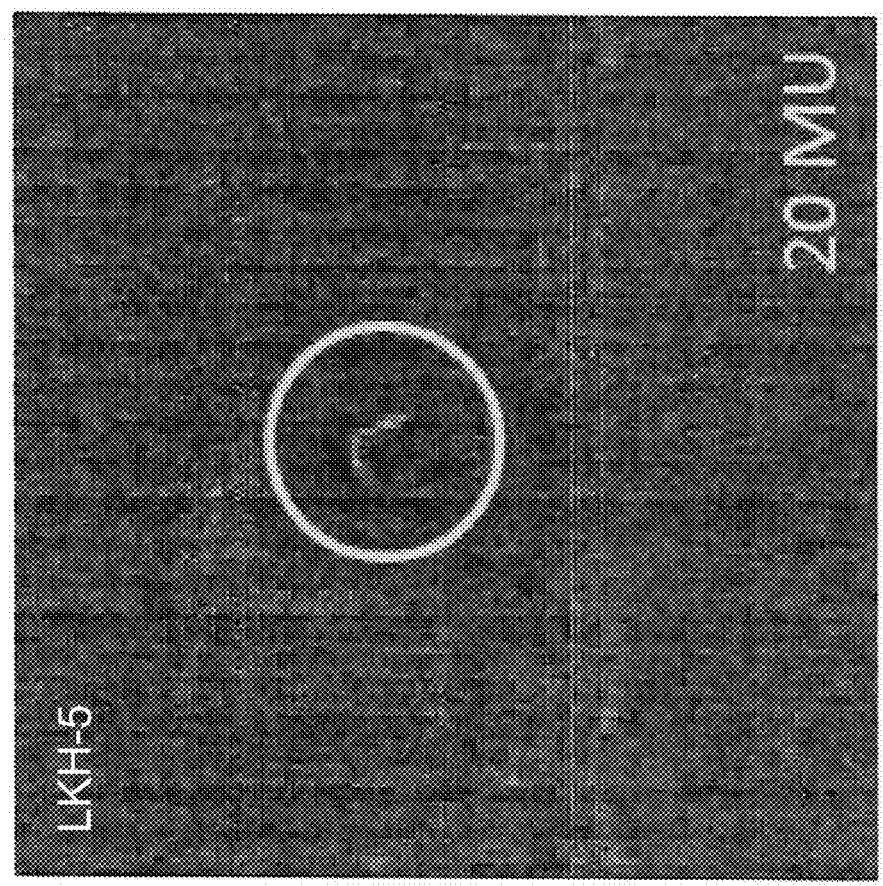
Figure 13:
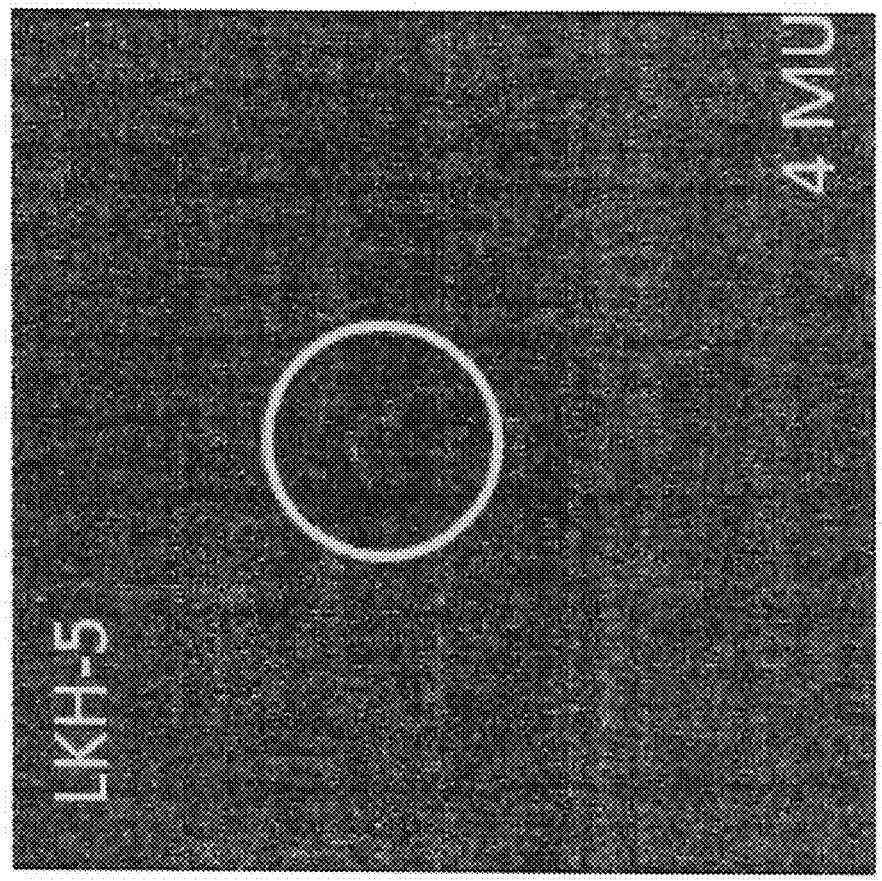

FIG. 13 shows two median filter corrected images for 4 MU (left) and 20 MU (right) 6×FFF exposures using the LKH-5 detector. The median filter size was defined as that which produced the maximum PSR in FIG. 12 (1×40 pixels).

Figure 14:
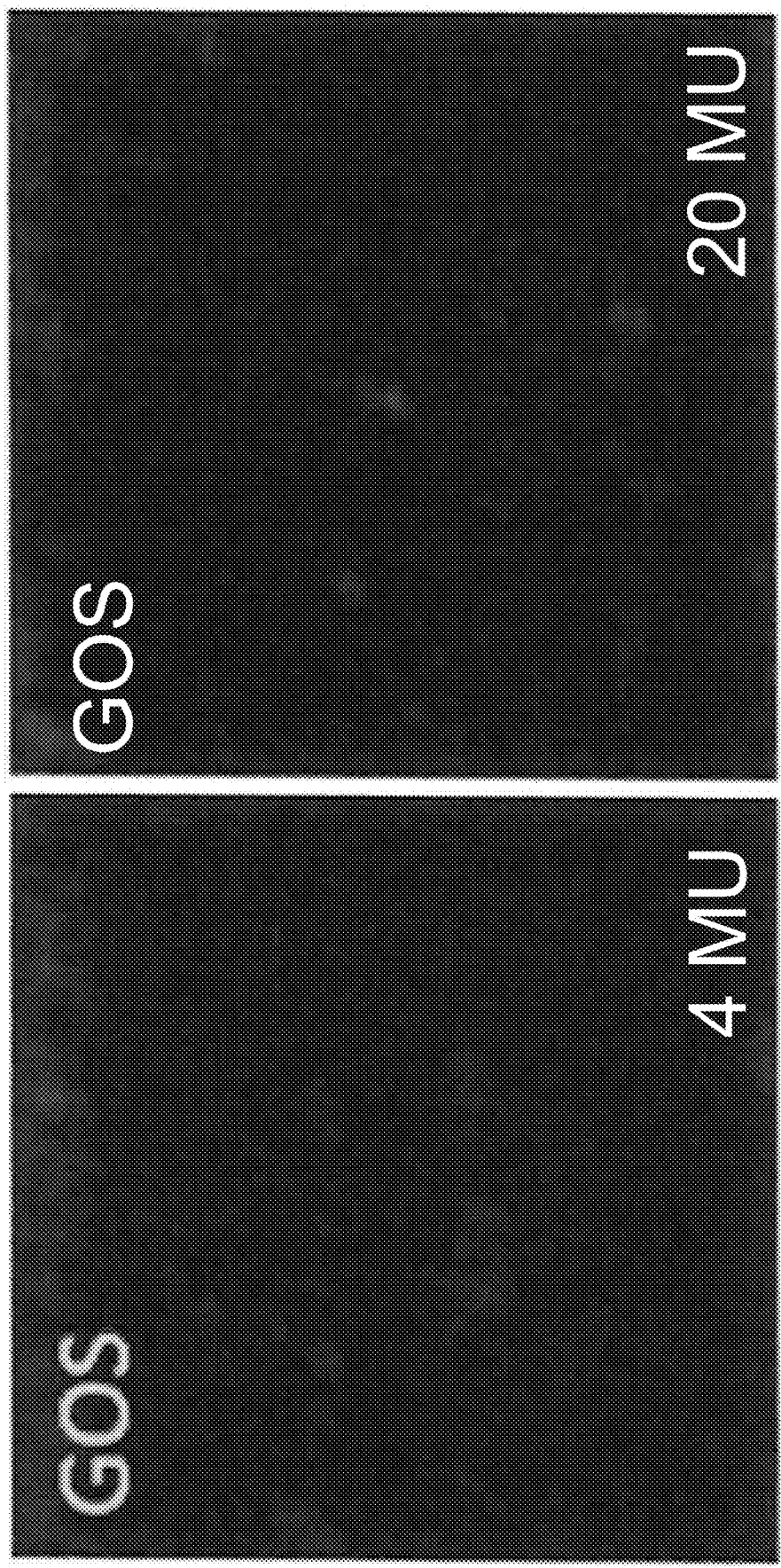

FIG. 14 shows two 133×133 pixel ROIs of the NCC maps of the median filter corrected images for 4 MU (left) and 20 MU (right) 6×FFF exposures using the GOS detector.

Figure 15:
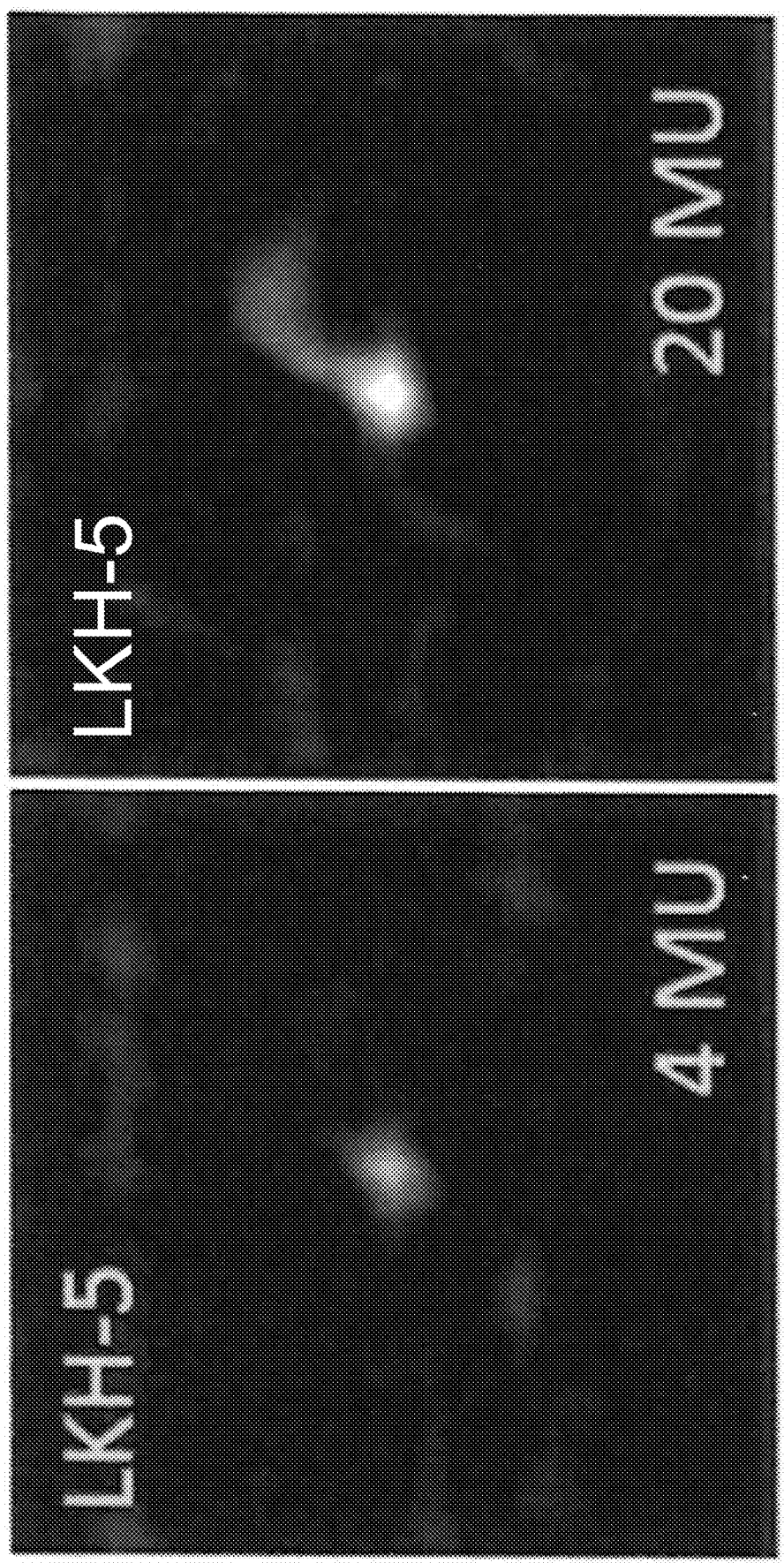

FIG. 15 shows two 133×133 pixel ROIs of the NCC maps of the median filter corrected images for 4 MU (left) and 20 MU (right) 6×FFF exposures using the LKH-5 detector.

Figure 16:
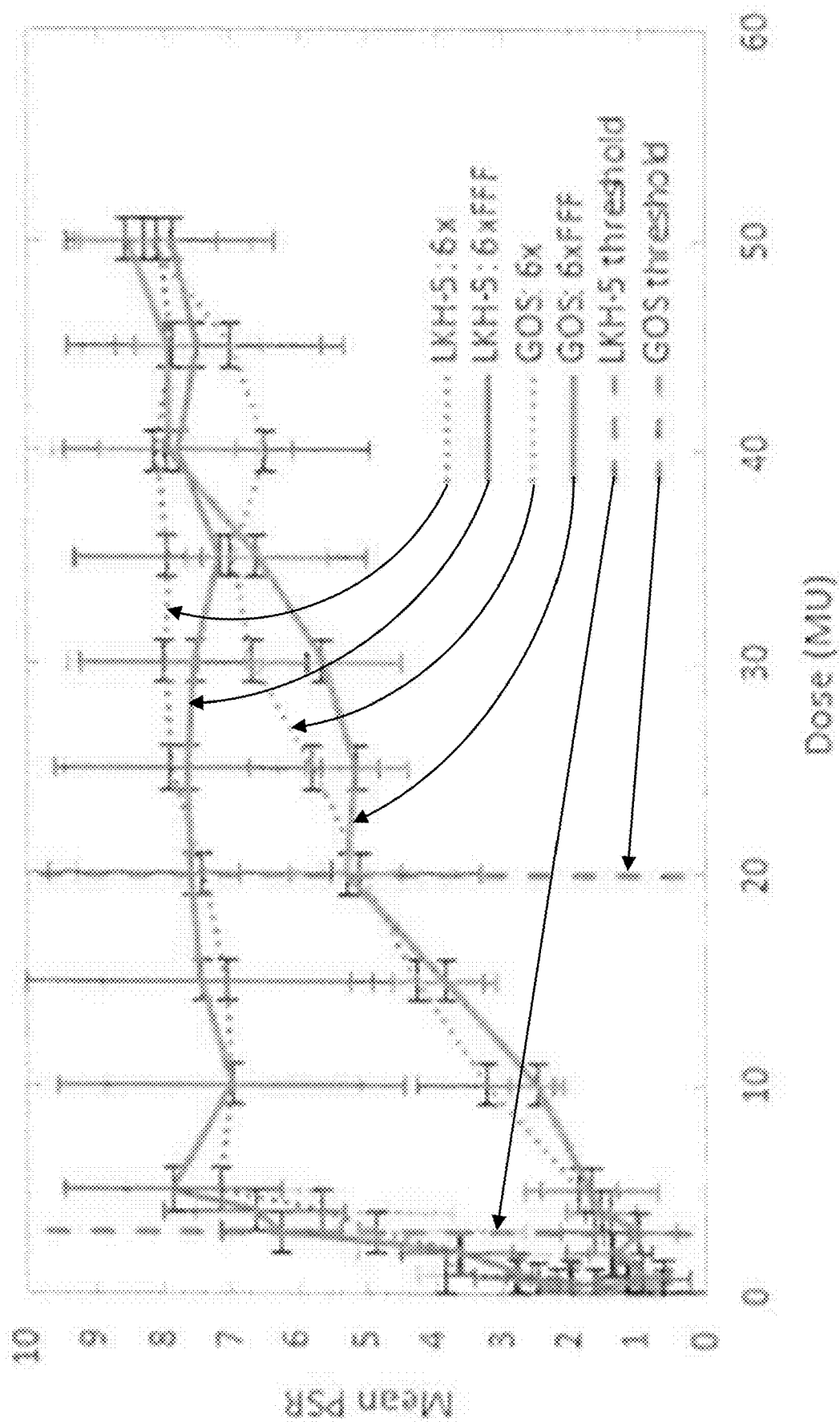

FIG. 16 shows a graph of a comparison of PSR for various doses for the LKH-5 and GOS detectors using 6× and 6×FFF modes of operation. The dashed, vertical lines describe the threshold of human detectability for the median filter corrected images.

Figure 17:
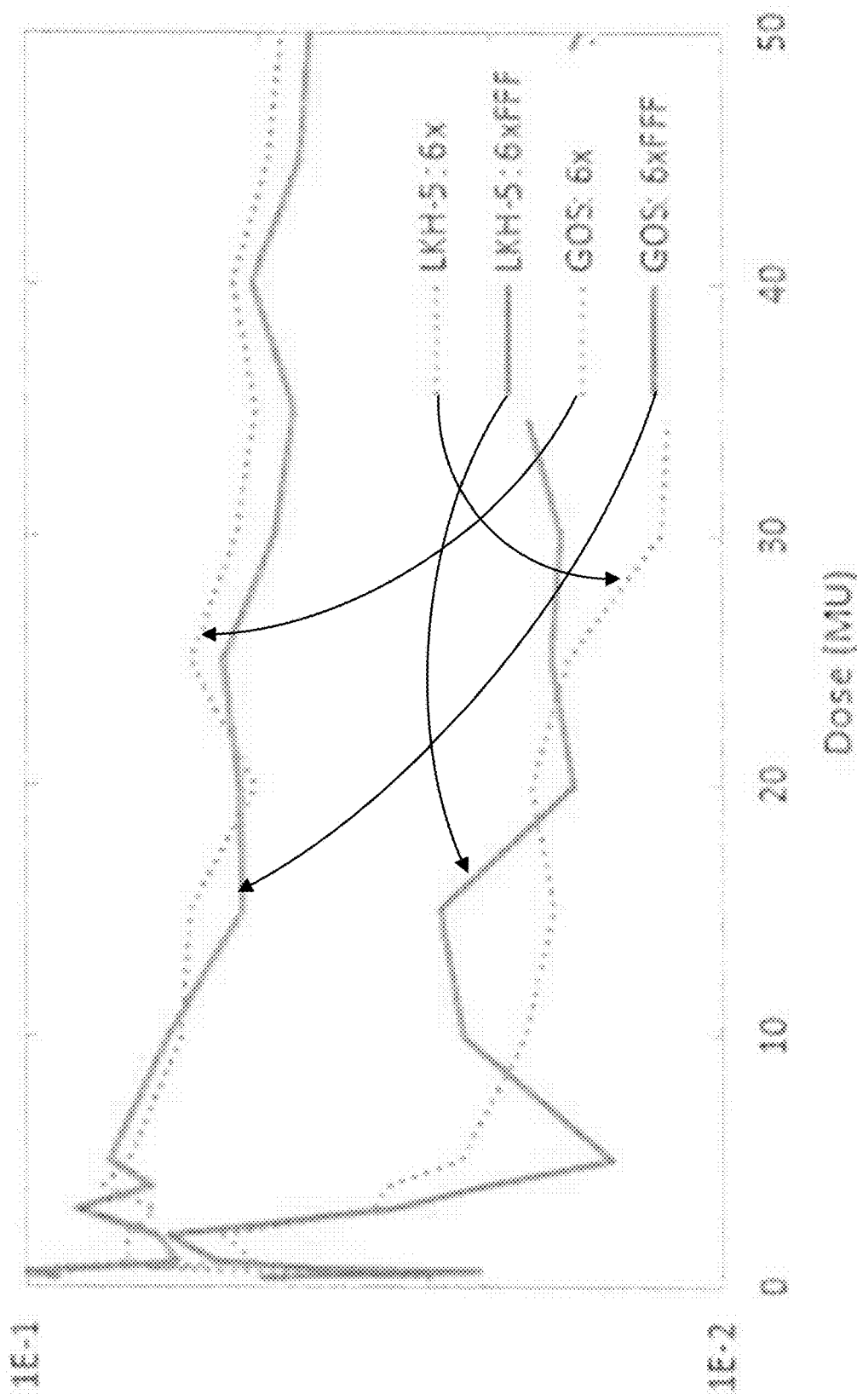

FIG. 17 shows a graph of a comparison of SoS normalized to mean for the NCC maps for various doses for the LKH-5 and GOS detectors using 6× and 6×FFF modes of operation.

Figure 18:
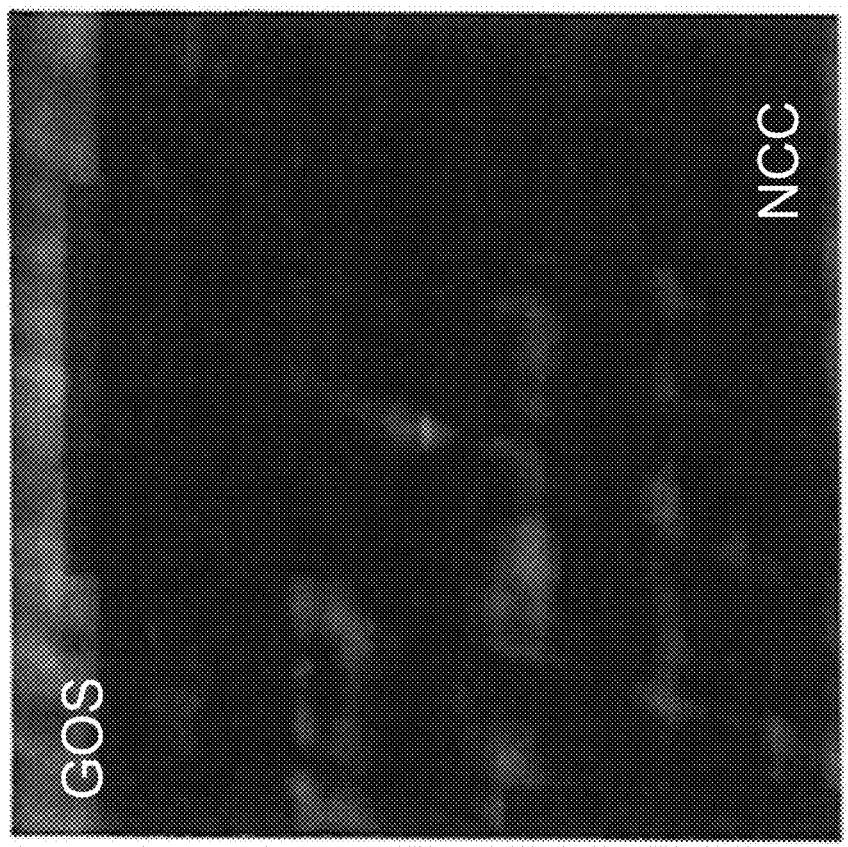
Figure 18:
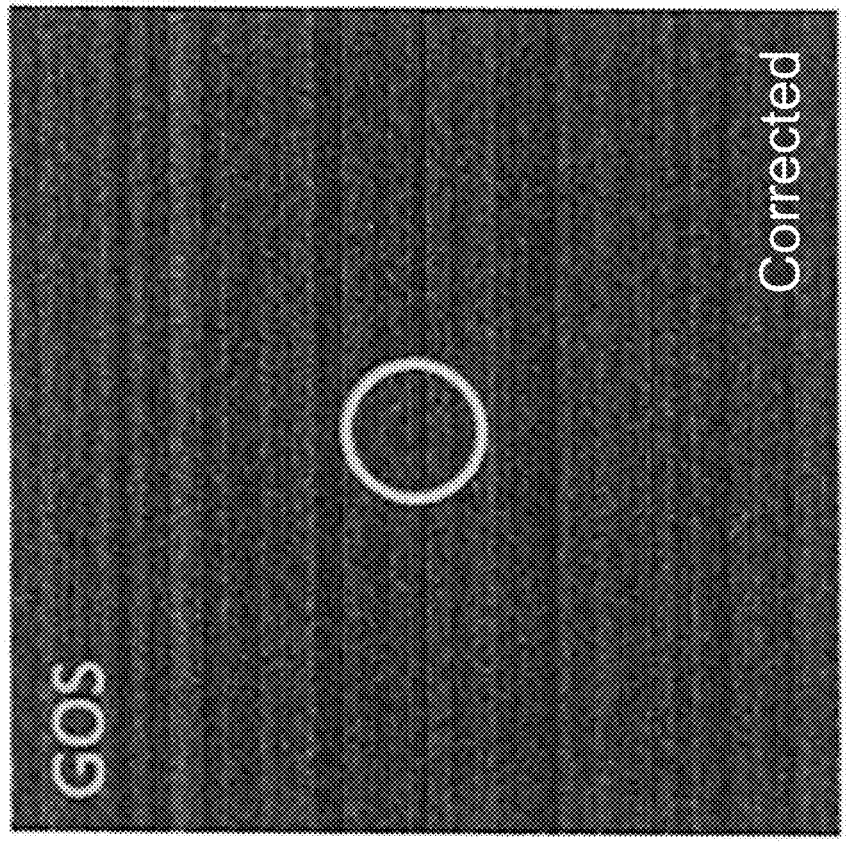

FIG. 18 shows a median filter corrected blocked MLC image (left) and template-matched NCC intensity map (right) for a 4-layer MLI configurations for the GOS detector. Acquisition doses were 10 MU for the GOS MLI detector.

Figure 19:
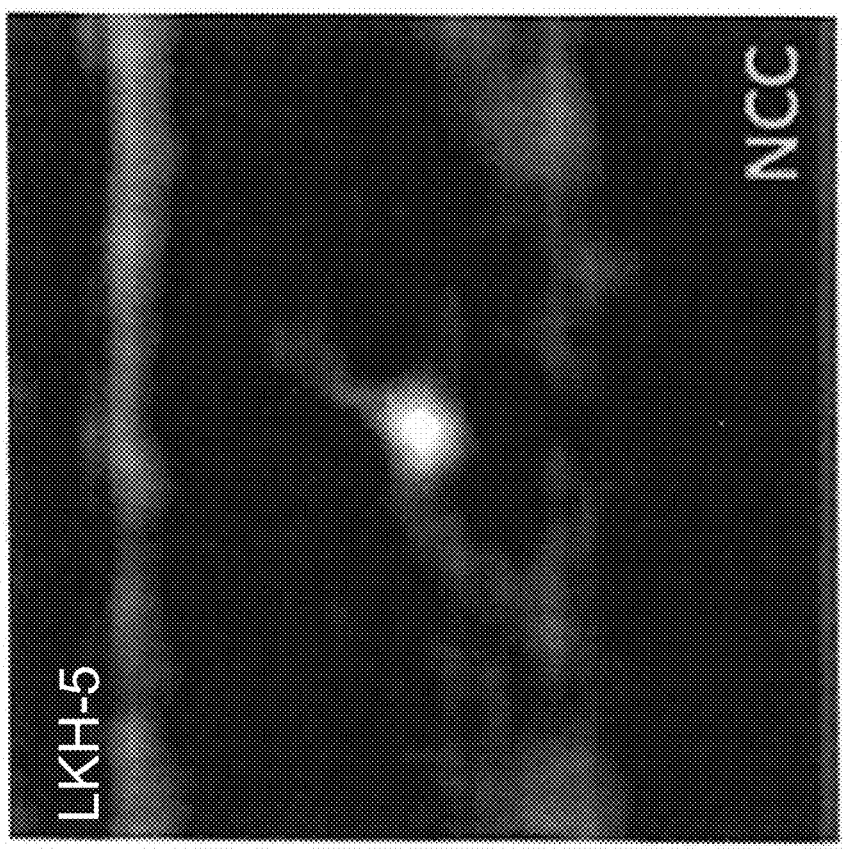
Figure 19:
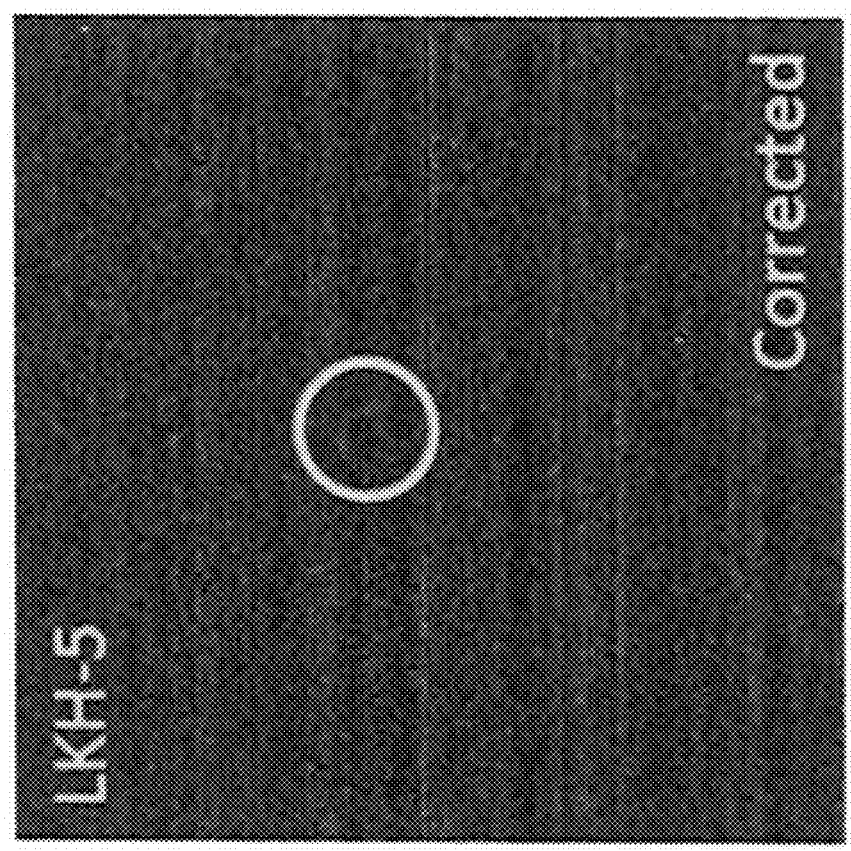

FIG. 19 shows a median filter corrected blocked MLC image (left) and template-matched NCC intensity map (right) for a 4-layer MLI configurations for the LKH-5 based detector. Acquisition doses were 2 MU for the LKH-5 MLI detector.

Figure 20:
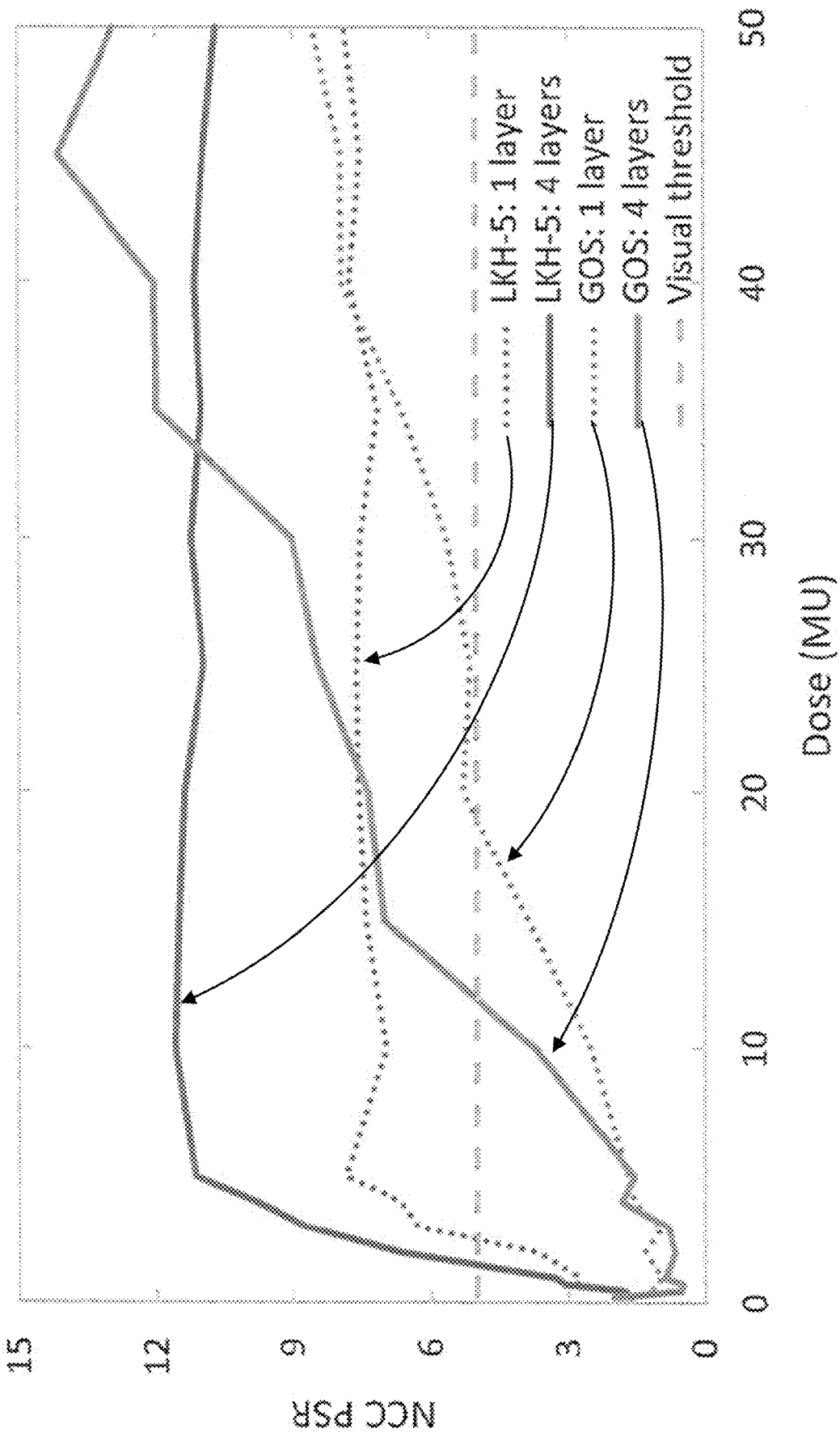

FIG. 20 shows a graph of the comparison of NCC PSR as a function of dose for 6×FFF acquisitions using either 1 or 4 layers of an LKH-5 or GOS based detector. The gray dashed line represents the empirically defined visual threshold.

DETAILED DESCRIPTION

As described above, tumor tracking can be helpful to ensure that particular tissue sites (e.g., tumors) are actually receiving the radiation therapy beam, while other tissue sites that are not intended to receive radiation (e.g., the heart) are not receiving the radiation therapy beam. In some cases, tumor tracking can be done using a radiation detector (e.g., an electronic portal imaging device) that is configured to image a beam's-eye-view ("BEV") of the radiation therapy beam. However, this BEV imaging is severely compromised when targets are not within the exposed region defined by the multi-leaf collimator ("MLC") thereby making effective tracking of the tumor and thus desired radiation treatment difficult. For example, in prostate treatment plans, implanted fiducial markers (e.g., those detectable by a radiation detector) are blocked by the MLC for up to 36-44% of control points. As another example, it was found that imaging even at an interval of 10 seconds yielded a dose violation rate of 19.5%.

While some have theorized mitigating strategies, these proposed solutions have largely been inadequate. For example, one proposed mitigating strategy is treatment re-planning to ensure fiducial marker visibility. However, in some cases, this can prevent a desired radiation treatment from being implemented (e.g., by adjusting the radiation treatment plan away from the most effective plan), and can add considerable time (e.g., computing time) to determine alternative plans. In some cases, there may not even be a single plan that can prevent the fiducial marker from being located outside the BEV of the radiation therapy beam during treatment. As another example, a second proposed mitigating strategy is using kilovoltage ("kV") on-board imagers ("OBI") that may better discern anatomical landmarks within the BEV as compared to other electronic portal imaging devices. However, while these OBIs may provide better images, there are still downsides to these configurations. For example, they require the use of kilovoltage X-rays, and the anatomical landmarks as well as the fiducial markers are still unable to be tracked if they are located outside the BEV. Additionally, even if a landmark is visible in the BEV, while the fiducial marker is not (e.g., corresponding with the tumor), and the position of the fiducial marker cannot be appropriately extrapolated from the tracking of the visible landmark at least because the fiducial marker has moved along an unknown trajectory (e.g., a non-linear trajectory).

Some non-limiting examples of the disclosure address these issues (and others) by providing improved systems and methods for tissue tracking with radiation therapy beams. For example, some non-limiting examples of the disclosure leverage the radiative leakage through the multi-leaf collimator (MLC) of a radiation therapy system, which is typically quantified at approximately 1-2%—a level that is effective in protecting healthy tissue—to locate and track the location of a radiation fiducial. In particular, some non-limiting examples of the disclosure provide a multi-detector imaging system that includes at least a first detector and a second detector. The first detector is configured to acquire imaging data when a radiation fiducial of a patient is located within an attenuated periphery of the radiation therapy beam, while the second detector is configured to acquire imaging data to track the radiation fiducial when the radiation fiducial is located outside an attenuated periphery of the radiation therapy beam. In some cases, the first detector can be tuned to the intensity level that corresponds to the portion of the radiation therapy beam that is within the attenuated periphery of the radiation therapy beam. In other cases, the first detector may not need to be tuned, at least because the intensity level of the radiation therapy beam within the attenuated periphery of the radiation therapy beam is sufficient to detect and track the radiation fiducial when the radiation fiducial is located within the attenuated periphery of the radiation therapy beam.

In some non-limiting examples, the first detector can be tuned to the attenuated intensity level that corresponds to the portion of the radiation therapy beam that is attenuated (e.g., 1-2% of the intensity level of that within the attenuated periphery of the radiation therapy beam). For example, the gain of the second detector can be increased to a value that is higher than the gain of the first detector. In some configurations, the second detector can be arranged more distally relative to the radiation source that emits the radiation therapy beam than the first detector. In some non-limiting examples, because the radiation fiducial can be detected and tracked irrespective of its position within or outside of the attenuated periphery of the radiation therapy beam, better radiation treatment plans can be realized. For example, optimized radiation treatment plans do not have to be undesirably manipulated in order to force the radiation fiducial to be within the BEV. As another example, faster treatment times can be realized at least because the treatment sessions do not need to be frequently stopped to validate the radiation fiducial location.

Figure 1:
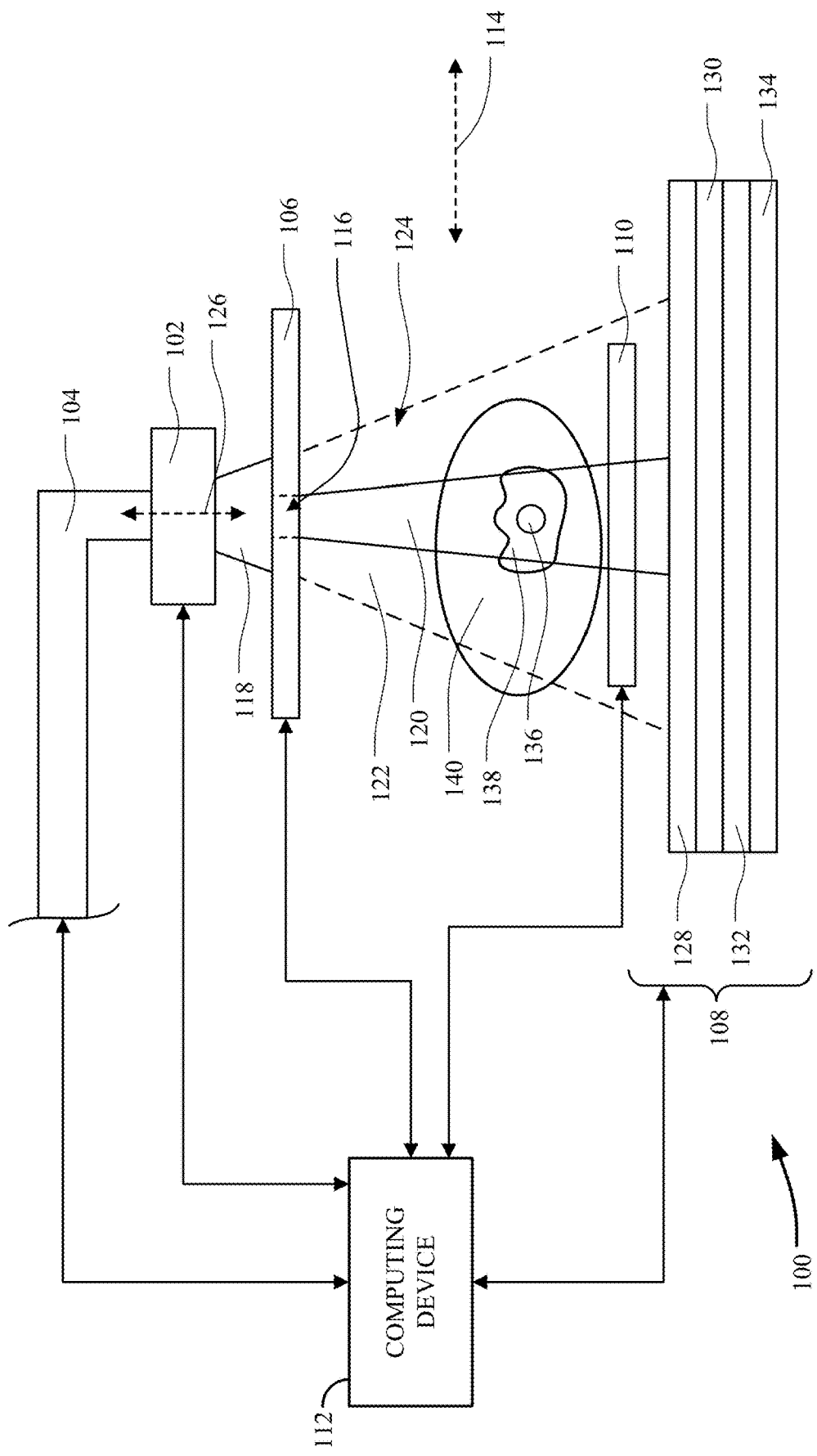
FIG. 1 shows a schematic illustration of a radiation therapy system.

FIG. 1 shows a schematic illustration of a radiation therapy system 100. The radiation therapy system 100 can include a radiation source 102, supported by a gantry 104 that is moveable, an adjustable collimator 106, a radiation therapy imaging system 108, a table 110 that supports a patient, and a computing device 112. The radiation source 102 can be an X-ray beam forming assembly configured to emit X-rays, or in other cases, the radiation source 102 can be a linear accelerator ("LINAC") or other particle accelerator configured to accelerate particles (e.g., electrons, protons, etc.), such as, a cyclotron (e.g., a synchrotron). As shown, the computing device 112 is in communication with the radiation source 102, and thus the computing device 112 can selectively control the radiation source (e.g., by turning on the radiation source 102 to emit a radiation beam or by turning the radiation source 102 off to stop the radiation source 102 from emitting the radiation beam).

The radiation source 102 is supported by a gantry 104 that is in communication with the computing device 112. The gantry 104 is moveable so that when the gantry 104 moves, the radiation source 102 moves with the gantry 104. The gantry 104 can be implemented in different ways. For example, the gantry 104 can be a cylinder gantry, a ring gantry, a C-arm gantry, while in other cases, the gantry 104 can be a housing that is coupled to a robot arm (e.g., where the robot arm moves the gantry 104 and thus the radiation source 102). As shown, the computing device 112 is in communication with the gantry 104 and can control the positioning of the gantry 104. For example, such as when the gantry 104 is rotatable about a pivoting axis 114 that is substantially perpendicular (e.g., deviating by less than 10%) to an axial axis that intersects the radiation source 102 and the imaging system 108 and is substantially parallel to a surface of the imaging system, the computing device 112 can cause the gantry 104 to rotate about the pivoting axis 114 to realize different radiation beam paths (e.g., according to a radiation treatment plan).

The adjustable collimator 106 may include a plurality of independently controllable leaves (not shown) that can collectively adjust the radiation attenuation profile of the adjustable collimator 106 (e.g., how a radiation beam is attenuated as it passes through the adjustable collimator 106). In the illustrated, non-limiting example shown in FIG. 1, the plurality of independently controllable leaves of the adjustable collimator 106 can define an opening 116 that can at least partially define the radiation attenuation profile of the adjustable collimator 106. In particular, because each of the independently controllable leaves are formed out of a radiation absorbing material (e.g., lead, tungsten, etc.), as a radiation beam 118 emitted by the radiation source 102 passes through the adjustable collimator 106, the radiation beam 118 is attenuated when it passes through the independently controllable leaves, while the radiation beam 118 is attenuated at a substantially smaller amount (if at all) when it passes through the opening 116. In the illustrated, non-limiting example, a first portion 120 of the radiation beam 118 is not attenuated by the adjustable collimator 106, while a second portion 122 of the radiation beam 118 is attenuated by the adjustable collimator 106.

In the illustrated, non-limiting example, the second, attenuated, portion 122 is located at or forms a periphery 124 of the radiation therapy beam 118, which is defined by the attenuation profile of the adjustable collimator 106. This periphery 124 can extend around a portion of an axial axis or isocenter 126 that extends along a path from the radiation source 102 to the imaging system 108 (and along the radiation therapy beam 118). The first portion 120 of the radiation therapy beam 118 may be referred to as the "open" portion when the collimator 106 does not attenuate the beam within the opening 116. Whether the opening 116 includes some amount of attenuation or not, the first portion 120, which is illustrated as arranged inside the periphery 124 or second portion 122, has a first intensity that is greater than a second intensity of the second portion 122/periphery 124 of the radiation therapy beam 118. In particular, the second intensity of the second portion 122 of the radiation therapy beam 118 can be between about (e.g., ±10% from a particular value) 1% and about 2% of the first intensity of the first portion 120 of the radiation therapy beam 118. In some cases where the collimator 106 does not attenuate along the opening 116, the first portion 120 or "open" portion of the radiation beam 118 can be defined as a full intensity radiation beam having an intensity that is substantially similar to the intensity of the radiation beam 118 prior to passing through the adjustable collimator 106, while the second portion 122 of the radiation beam 118, forming the periphery 124 in the illustrated example, can be defined as an attenuated intensity radiation beam having an intensity that is less than the intensity of the radiation beam 118 prior to passing through the adjustable collimator 106. In some non-limiting examples, the portion 122 of the radiation therapy beam 118 can be defined as radiative leakage through one or more leaves of the adjustable collimator 106, or through gaps between adjacent leaves of the adjustable collimator 106.

Although the adjustable collimator 106 has been described as having an opening 116 that passes through the entire adjustable collimator 106, in other cases, the adjustable collimator 106 can include or can rather have (as opposed to the opening 116) a concavity, or other attenuation profile defined by the plurality of independently moveable leaves. In this case, for example, one or more of the independently controllable leaves can extend along an entire width of the radiation therapy beam 118. Although each of the portions 120, 122 of the radiation therapy beam 118, which are coaxially about the axial axis 126, have been illustrated as having a cone shape, in other configurations, the shape of the first portion 120 of the radiation therapy beam 118 can be adjusted (e.g., by adjusting the collective positioning of the independently controllable leaves of the adjustable collimator 106). For example, an axial cross section of the first portion 120 of the axial axis 126 can have various different shapes, which can include a star, an octagon, or other shapes including an amorphous shape (e.g., a shape for use with an intensity modulated treatment).

As shown, the computing device 112 can be in communication with the adjustable collimator 106, and in particular, can be in communication with the plurality of independently controllable leaves. In this way, the computing device 112 can control the collective positioning of the independently controllable leaves thereby adjusting the attenuation profile of the adjustable collimator 106 (e.g., adjusting the shape and size of the opening 116). For example, a respective actuator can be moveably coupled to each corresponding independently controllable leaf of the adjustable collimator 106. In this way, the computing device 112 can selectively move each independently controllable leaf by translating (e.g., retreating or advancing) a respective actuator. The adjustable collimator 106 can be implemented in different ways. For example, the adjustable collimator 106 can be a multi-leaf collimator ("MLC"), while in other cases, the adjustable collimator 106 can have a collective shape of a bowtie with independently controllable leaves that each have a portion having a bowtie shape.

As shown, the radiation therapy system 100 can include a radiation therapy imaging system 108. The radiation therapy imaging system 108 can include radiation detectors 128, 130. In some non-limiting examples, the radiation detector 128 is situated above the radiation detector 130 so that the radiation detector 128 interacts with the radiation therapy beam 118 before the radiation detector 130. In other words, the radiation detector 130 is positioned more distally to the radiation source 102 than the radiation detector 128. Each radiation detector 128, 130 includes a plurality of sensing elements that are each configured to sense radiation that interacts with the respective sensing element. In some non-limiting examples, the radiation detector 128 can have a number of different layers that can collectively define each sensing element of the plurality of sensing elements of the radiation detector 128. For example, the radiation detector 128 can include a copper conversion layer that is situated on top of a scintillator layer (e.g., that includes gadolinium oxysulfide ("GOS")), which is situated on top of a light conversion layer (e.g., visible light) such as a photodiode array, which is situated on top of a (lead) backing layer. Thus, each sensing element can be include for each photodiode, a portion of the (copper) conversion layer corresponding with the respective photodiode, and a portion of the scintillator layer corresponding with the respective photodiode. In some configurations, the radiation detector 128 does not include the lead backing layer (or any lead layer). In this way, the lead backing layer does not undesirably impact the delivery of radiation to the subsequent detector (e.g., the next detector directly below the previous detector).

Similarly to the radiation detector 128, in some configurations, the radiation detector 130 can also include a number of layers that can also collectively define each sensing element of the plurality of sensing elements of the radiation detector 130. For example, the radiation detector 130 can include a (copper) conversion layer that is situated on top of a scintillator layer, which is situated on top of a light conversion layer (e.g., visible light) such as a photodiode array, which is situated on top of a (lead) backing layer. In some non-limiting examples, the scintillator layer of the radiation detector 130 can be a pixelated scintillator having individual (square) elements each corresponding to a respective photodiode of the photodiode layer. In some cases, the pixelated scintillator can include a LKH-5 scintillating glass material. In some non-limiting examples, the (copper) conversion layer can be removed, and in some cases, the (lead) backing layer can be removed as well. The removal of the backing layer (e.g., a lead backing layer) can be particularly advantageous in configurations in which there are two or more radiation detectors. For example, in some non-limiting examples, the imaging system 108 can include additional radiation detectors 132, 134 which can be implemented as either of the detectors 128, 130. The detector 134 is positioned more distally relative to the radiation source 102 than each of the detectors 128, 130, 132. The detectors 128, 130, 132 can all have a backing layer (e.g., a lead backing layer) removed (e.g., each of these detectors not having a backing layer) so that radiation is not attenuated by the backing layers, and can rather be sensed by more distal detectors (e.g., detectors positioned directly blow each other). In some cases the detector 134 can have a backing layer (e.g., a lead backing layer), which can attenuate any leftover radiation that has not been sensed by the radiation detectors.

In some non-limiting examples, some of the detectors 128, 130, 132, 134 can have their conversion layer (e.g., a copper conversion layer) removed (e.g., these detectors not including a conversion layer, different from the scintillating layer), which may allow for better radiation sensing. For example, the detectors 130, 132, 134 that are all situated below (and more distally away from the radiation source 102) than the detector 128 can have the conversion layer (e.g., the copper conversion layer) removed. In this way, such as when the detectors 132, 134 are implemented as the detector 130, the copper conversion layer does not undesirably impact radiation sensing by a detector that is positioned directly above another detector (e.g., the detectors 130, 132).

In some non-limiting examples, although the detectors 128, 130, 132, 134 have been described as having an array of photodiodes as the light conversion layer, in other configurations other light conversion elements can be used as appropriate in place of the photodiodes, such as phototransistors, etc. In some non-limiting examples, the detectors of the imaging system 108 can be packaged within a single housing, and mounted below the table 110 (e.g., below the patient). In some non-limiting examples, rather than having scintillator layers, any of the detectors 128, 130, 132, 134 can be implemented as photon-counting detectors. In this case, the photon-counting detector also includes a plurality of sensing elements, each of which are configured to discriminate individual x-ray photons and their corresponding energies.

In some non-limiting examples, the plurality of sensing elements for each detector 128, 130, 132, 134 can define a respective sensing area of the corresponding detector. As shown, the sensing area of each detector 128, 130, 132, 134 is identical to each other, but in other configurations, the sensing area of each detector 128, 130, 132, 134 can be substantially similar to each other (e.g., deviating by ±10%). In some non-limiting examples, the number of the plurality of sensing elements for each detector 128, 130, 132, 134 can be the same, or substantially the same to each other. As shown, the sensing areas of the detectors 128, 130, 132, 134 are coaxial with the axial axis 126 and thus the sensing areas of the detectors 128, 130, 132, 134 completely overlap. In other configurations, however, the sensing areas of the detectors 128, 130, 132, 134 can substantially overlap (e.g., partially overlapping). In some non-limiting examples, although the detectors 128, 130, 132, 134 are illustrated as being stacked on top of each other, with opposing surfaces contacting each other (e.g., the lower surface of the detector 128 contacting the upper surface of the detector 130), in other cases, adjacent detectors can be separated by an axial gap along the axial axis 126.

In some non-limiting examples, each detector 128, 130, 132, 134 can have properties (e.g., the type of scintillator used) that define its respective dynamic range, or in other words, the range defined between the minimum value the detector can sense and the maximum value the detector can sense. In this case, the minimum value and the maximum value can be monitor units ("MUs") or can be other units such as radiation per second. In some cases, each detector 128, 130, 132, 134 can be tuned to sense particular radiation value ranges (e.g., MU ranges) by leveraging each detector's intrinsic dynamic range. For example, the gain of each of the detectors 128, 130, 132, 134 can be adjusted (e.g., increased or decreased) to adjust the given detectors sensitivity to particular radiation value ranges, which can be defined by its respective dynamic range. In this way, the detectors 128, 130, 132, 134 can be tuned to sense more specific radiation ranges that do not necessarily overlap. For example, the detector 128 can be tuned to sense the portion 120 of the radiation beam 118, while not sensing (or not appropriately sensing) radiation from the portion 122 of the radiation beam 118. Alternatively, the detector 130 can be tuned to sense the portion 122 of the radiation beam 118, while not sensing (or not appropriately sensing) radiation from the portion 120 of the radiation beam 118. In some cases, the gain of the radiation detector 130 can be higher than the gain of the detector 128. In this way, because the radiation is at a sufficiently high level at the portion 120 of the radiation beam 118, the gain of the detector 128 can be low (or significantly lower), whereas the radiation is at a fairly low level at the portion 122 and thus the gain can be high (or significantly higher).

In some non-limiting examples, the detectors 132, 134 can be implemented as the detector 130. In this case, for example, the detectors 130, 132, 134 can all be tuned to the same radiation range (or substantially the same radiation range). Additionally, the detectors 130, 132, 134 can all have the same gain or substantiality the same gain. In this way, as will be described in more detail below, residual radiation not sensed by the detector 130 can be sensed by the detectors 130, 132. In this way, imaging data from each detector 130, 132, 134 can be combined (e.g., added) to construct an image that can have a higher resolution than an image constructed using imaging data from only the detector 130.

Although in the illustrated non-limiting example the imaging system 108 includes detectors 128, 130, 132, 134, in other configurations the imaging system 108 can include fewer or more detectors. For example, in one configuration, the imaging system 108 can include only the detectors 128, 130, while in other cases, the imaging system 108 can include additional detectors (e.g., 5, 6, 7, etc., detectors total).

As shown, the computing device 112 is in communication with the imaging system 108, and in particular is in communication with each detector of the imaging system 108. Thus, the computing device 112 is in communication with each of the detectors 128, 130, 132, 134 and can acquire imaging data from each of the detectors 128, 130, 132, 134.

In some non-limiting examples, the radiation therapy system 100 can include a table 110 that supports a patient. In some cases, the table 110 can be stationary, while in other case, the table 110 can be moveable. For example, the table 110 can be coupled to a robotic arm, or can be actuated to be advanced or retreated through, for example, a bore of the gantry 104. As shown, the computing device 112 can be in communication with the table 110, as appropriate, to selectively move the table 110 (e.g., with the patient thereon).

The computing device 112 can be implemented in different ways. For example, the computing device 112 can include typical components used such as a processor, memory, a display, inputs (e.g., a keyboard, a mouse, a graphical user interface, a touch-screen display, etc.), communication devices, etc. In some cases, the computing device 112 can simply be implemented as a processor. The computing device 112 can communicate with other computing devices and systems. In some non-limiting examples, the computing device 28 can implement some or all of the processes described below.

In the illustrated non-limiting example of FIG. 1, the radiation therapy system 100 can be used with a radiation fiducial marker 136 that can be sensed by the imaging system 108. The radiation fiducial maker 136 can have different sizes and shapes (e.g., a circle), and can be formed of different materials including radiation absorbing materials including radiation absorbing metals such as lead, gold, etc. As shown, the radiation fiducial marker 136 has been implanted into a tumor 138 of a patient 140 that is supported by the table 110. However, in other configurations, the radiation fiducial marker 136 can be placed on a surface of the skin of the patient 140 that is in alignment with the tumor 138 along the axial axis 126. Although the illustrated non-limiting example has been described has having the radiation fiducial maker 136 located within the tumor 138, in other configurations, the radiation fiducial maker 136 can be placed to track other tissue sites desired to be irradiated, or in some cases, tissue sites that are not desired to be irradiated. For example, the radiation fiducial marker 136 can be coupled to a surface of the skin that is axially aligned (along the axial axis 126) with a tissue site that is not desired to be irradiated (e.g., a tissue site overly sensitive to radiation exposure, an organ, such as the heart, the liver, or other sub-organ structures). In some cases, rather than having a single radiation fiducial marker 136, the radiation therapy system 100 can include a plurality of radiation fiducial markers, which can have different shapes and sizes. In this way, for example, the plurality of radiation fiducial makers 136 can be axially aligned along the periphery of the tumor. In other cases, a first radiation fiducial marker can be axially aligned with the tissue site that is desired to be irradiated, while a second radiation fiducial marker can be axially aligned with a tissue site that is not desired to be irradiated. In some non-limiting examples, the radiation fiducial marker 136 can include an adhesive layer to couple the radiation fiducial marker to a surface of the patient.

Regardless of the implementation of the radiation fiducial makers 136, the imaging system 108 is configured to track the position of the radiation fiducial marker regardless of whether the radiation fiducial marker is positioned within the portion 120 of the radiation beam 118 or positioned within the portion 122 of the radiation beam 118. For example, as shown, when a portion of the radiation fiducial marker 136 is located within the first portion 120 of the radiation beam 118, the detector 128 can track the position of the radiation fiducial marker 136 within an axial plane along the axial axis 126. When the tumor 138 and at least a portion of the radiation maker 136 move (e.g., from patient movements such as respiratory motion) from the portion 120 of the radiation beam 118 and into the portion 122 of the radiation beam 118, the detector 130 (and the other detectors 132, 134) can track the position of the radiation fiducial marker 136 within an axial plane along the axial axis 126.

In some cases, the computing device 112 can receive dimensional data of the tumor 138 (or other tissue) that the radiation fiducial maker 136 is intended to track, which can be used to adjust the operation of the radiation therapy system 100 (e.g., to stop the emission of the radiation therapy beam 118). For example, if the computing device 112 receives a width of the tumor 138 that extends along the axis 114, and the width of the tumor 138 is related to the position of the radiation fiducial marker 136, the computing device 112 by determining the location of the radiation fiducial marker 136 can thus determine the width boundary of the tumor 138 at a particular location of the radiation fiducial marker 136. In some cases, the dimensional data can include the peripheral boundary of the tumor 138 (either within a cross-section of the tumor 138 along the axial axis 126, or a 2D projection of the tumor 138 from the axial axis 126). In this way, the peripheral boundary of the tumor 138 can be related to the location of the radiation fiducial marker 136, and thus the computing device 112 by determining the location of the radiation fiducial marker 136 can thus determine the periphery boundary of the tumor 138 at a particular location of the radiation fiducial marker 136. In some non-limiting examples, these processes can track other radiation fiducial markers that are aligned with other structures (e.g., organs).

Figure 2A:
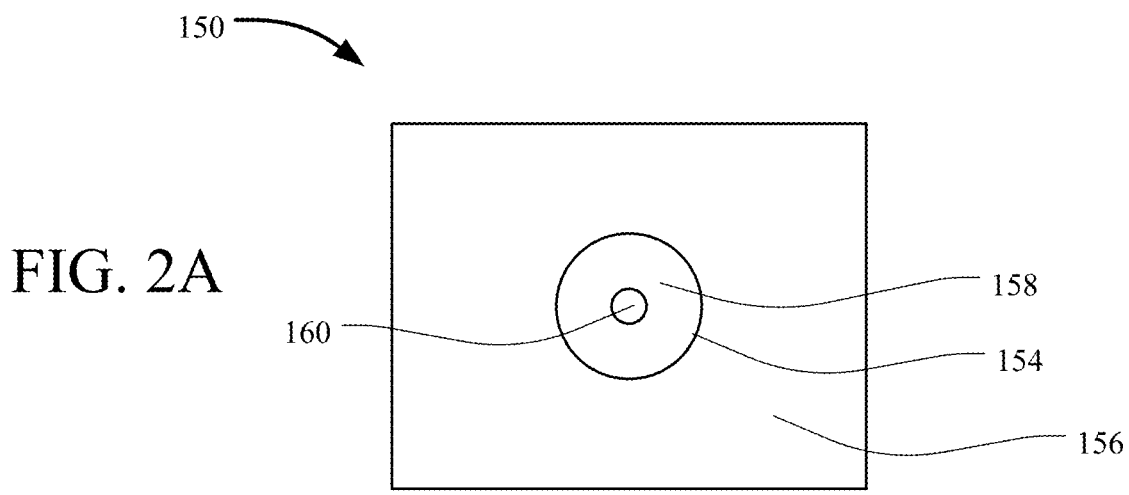
FIG. 2A show an illustration of an example of a reconstructed image.
Figure 2B:
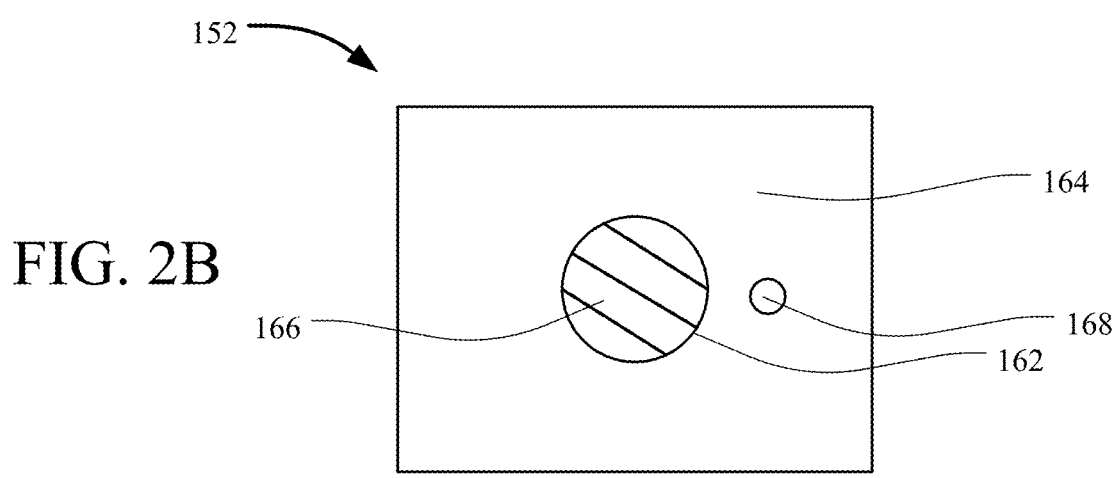
FIG. 2B shows another illustration of an example of a reconstructed image.

FIGS. 2A and 2B show illustrations of examples of constructed images 150, 152 from imaging data acquired from the detectors 128, 130, respectively. As shown in FIG. 2A, image 150 has a peripheral edge 154 that corresponds to the attenuation periphery 124 of the radiation therapy beam 118. While the peripheral edge 154 is illustrated as being a circle, in other configurations, such as when the attenuation profile of the adjustable collimator 106 is changed, the peripheral edge 154 can have other shapes. The peripheral edge 154 of the image 150 separates regions 156, 158 of the image 150. The region 156 of the image 150 corresponds to the portion 122 of the radiation therapy beam 118, and is not particularly useful (e.g., the detector 128 is not tuned to these radiation intensity values, or in other words these radiation intensity values are too low to be sensed by detector 128). The region 158, however, corresponds to the portion 120 of the radiation therapy beam 118 and is useful (e.g., the detector 128 is tuned to these radiation intensity values, or in other words, these radiation values are within the dynamic range of the detector 128). Thus, when the radiation fiducial marker 136 is located within the portion 120 of the radiation beam 118, a mark 160 corresponding to the radiation fiducial marker 136 can appear in the region 158 of the image 150. In some cases, although the mark 160 is illustrated as a circle, corresponding to the radiation fiducial marker 136 being entirely located in the region 158 of the image 150, in other cases, if only a portion of the radiation fiducial marker 136 is positioned in the portion 120 of the radiation therapy beam 118, only that portion of the radiation fiducial marker 136 appears as a mark in the region 158 of the image 150 (e.g., a semi-circle).

As shown in FIG. 2B, image 152 also has an edge 162 that also corresponds to the attenuation periphery 124 of the radiation therapy beam 118 (and the peripheral edge 154 of the image 150). The edge 162 separates the image 152 into regions 164, 166. The region 164 of the image 152 corresponds to the portion 122 of the radiation therapy beam 118 and a mark 168 corresponding to the radiation fiducial marker 136 is visible in the region 164 of the image 152 (e.g., the detector 130 is tuned to these radiation intensity values, or in other words, these radiation values are within the dynamic range of the detector 130). The region 166 of the image 152, however, is not particularly useful and may appear a completely white (e.g., being oversaturated) with the pixels having a maximum value (e.g., the detector 130 is not tuned to these radiation intensity values, or in other words these radiation intensity values exceed the dynamic range of the detector 130). Similarly to the image 150, in some cases, although the mark 166 is illustrated as a circle, corresponding to the radiation fiducial marker 136 being entirely located in the region 158 of the image 150, in other cases, if only a portion of the radiation fiducial marker 136 is positioned in the portion 122 of the radiation therapy beam 118, only that portion of the radiation fiducial marker 136 appears as a mark in the region 164 of the image 152 (e.g., a semi-circle).

In some configurations, a computing device can process the images 150, 152 (or imaging data used to construct the images 150, 152). For example, a computing device can locate the edge 162 of the image 152 and segment out that portion from the image 152 leaving behind only the region 164 of the image 152. In other cases, the computing device can segment out the region 166 of the image 152 based on a predefined region. For example, such as when the size of the imaging surface of the detector 128 is smaller than the size of the imaging surface of the detector 130, the size of the imaging surface of the detector 128 can define a region of interest for the image 152. This region of interest can be used by a computing device to segment a region out of the image 152, which may make segmenting the image 152 faster. In some cases, the imaging data acquired from the detector 130 can exclude pixels defined by the region of interest. In other cases, rather than the region of interest being predefined, the computing device can locate the peripheral edge 154 of the image 150 to determine a region of interest, which can be used to segment out a portion of the image 152.

Figure 2C:
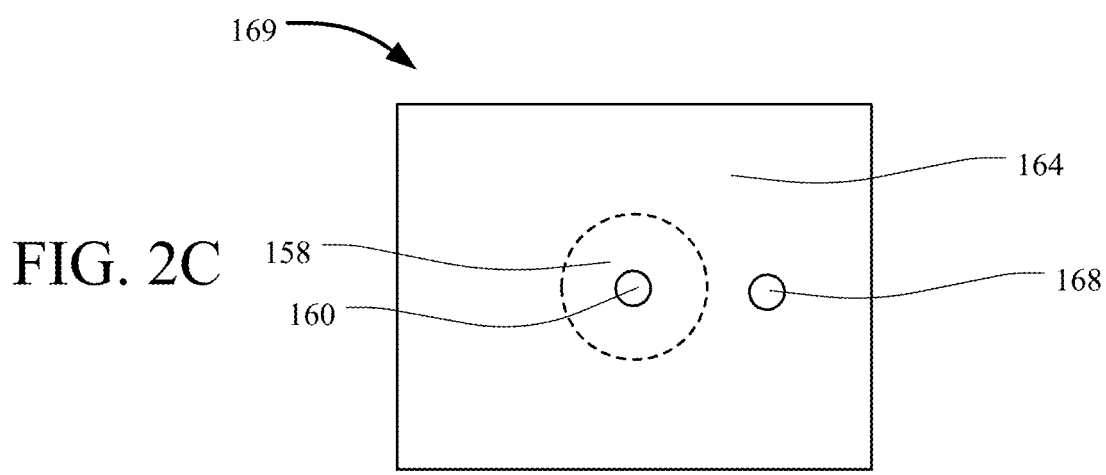
FIG. 2C shows yet another illustration of an example of a reconstructed image formed using the images of FIGS. 2A and 2B.

FIG. 2C also shows an illustration of an example of a combined image 169, combined from region 158 of the image 150 with region 164 of the image 152. In some cases, a computing device can superimpose the portion 158 of the image 150 onto the region 164 of the image 152 (e.g., after having segmented the images 150, 152). Although markers 160, 168 are shown in the combined image 169 each of which corresponds to the radiation fiducial marker 136, in some implementations, the markers 160, 168 are not going to appear in the combined image 169. However, in some cases, such as when there are other radiation fiducial markers, each mark can be shown in the combined image 169. In some non-limiting examples, a combined image 169 of the images 150, 152 can be formed in other ways. For example, a computing device can extract the marker 160 from the image 150 (e.g., by thresholding the image 150, by binarizing the image 150), determine the boundary of the marker 160, adjust the pixel values of the image marker 160 (e.g., within the boundary of the marker 160) such as increasing them, or enhancing them, adjusting a color of the pixels of the image marker 160 (e.g., to uniform color), and superimpose the image of the marker 160 on the second image 152 (or other image). The computing device can similarly extract the marker 166 from the second image 152, and superimpose the marker 166 on the image 150 (or other image).

Regardless of how the images 150, 152 are combined, a combined image (e.g., the combined image 169) can be presented on a display (e.g., of the computing device 112). In this way, the radiation fiducial marker 136 can be tracked on the display, which can allow a practitioner validate a tumor position, adjust the treatment, etc.

FIG. 3 shows an illustration of a side view of a radiation therapy imaging system 170, which is a specific implementation of the radiation therapy imaging system 108. As shown, the imaging system 170 can include imagers 172, 174. Each imager 172, 174 is tuned to sense different radiation ranges. For example, the imager 172 is configured to sense radiation within a radiation range that is higher than a radiation range of the imager 174. Similarly, the imager 174 is configured to sense radiation within a radiation range that is lower than the radiation range of the imager 172. In some cases, each imager 172, 174 has a different dynamic range. The imager 172 can include radiation detectors 176, 178, 180, 182 that each include a plurality of sensing elements, and that are each configured to sense radiation within the radiation range of the imager 174. In some cases, all the detectors 176, 178, 180, 182 have similar properties (e.g., the same number of sensing elements, the same sensing area, the same perimeter, etc.). In some non-limiting examples, each detector 176, 178, 180, 182 can be implemented as the detector 128. Although four detectors 176, 178, 180, 182 are illustrated, the imager 172 can have a smaller number of detectors, such as only having the detector 176.

The imager 174 can include radiation detectors 184, 186, 188, 190 that each include a plurality of sensing elements, and that are each configured to sense radiation within the radiation range of the imager 174. In some cases, all the detectors 184, 186, 188, 190 have similar properties (e.g., the same number of sensing elements, the same sensing area, the same perimeter, etc.). In some non-limiting examples, each detector 184, 186, 188, 190 can be implemented as the detector 130. Although four detectors 184, 186, 188, 190 are illustrated, the imager 174 can have a smaller number of detectors (or greater number of detectors), such as only having the detector 184, only having the detectors 184, 186, or having five, six, etc., detectors. In some non-limiting examples, the imagers 172, 174 can be electronic portal imaging detectors (EPIDs).

Each imager 172, 174 and each detector within the respective imager can be in communication with a computing device (e.g., the computing device 112). In this way, imaging data from multiple detectors having similar radiation sensing capabilities can be combined to construct an image having, for example, superior resolution than images constructed from only a single detector. For example, imaging data from each of the detectors 176, 178, 180, 182 can be combined (e.g., added together), while imaging data from each of the detectors 184, 186, 188, 190 can be combined (e.g., added together).

FIG. 4 shows an illustration of a top view of a radiation therapy imaging system 200, which is a specific implementation of the radiation therapy imaging system 108. The imaging system 200 can include radiation detectors 202, 204. The detector 202 is positioned above the detector 204, so that the detector 204 is positioned more distally away from a radiation source than the detector 202. The detectors 202, 204 each include a plurality of sensing elements, each of which is configured to sense radiation interacting with the respective sensing element. The first plurality of the sensing elements of the first detector 202 defines a sensing area 206, while the second plurality of sensing elements of the second detector 204 defines a sensing area 208. As shown, the sensing area 206 of the detector 202 is smaller than the sensing area 208 of the detector 204, and the sensing area 206 of the detector 202 has a shape (e.g., a square) that is different than a shape (e.g., a rectangle) of the sensing area 208 of the detector 204. In some cases, the detector 202 can have similar radiation sensing properties as the detector 128, while the detector 204 can have similar radiation sensing properties as the detector 130. In this way, because the detector 204 only senses the higher intensity portion of a radiation therapy beam (e.g., the portion 120 of the radiation therapy beam 118), the sensing area 206 of the detector 202 can be made smaller than the sensing area 208 of the detector 204. This can provide certain advantages that can include being more economical (e.g., decrease sensor footprint), providing faster image computation (e.g., less sensor elements to acquire imaging data from), and potentially higher image resolution from the detector 204 because, for example, a scintillating layer of the detector 202 does not absorb the radiation from the lower intensity portion of the radiation beam (e.g., the portion 122 of the radiation therapy beam 118).

In some configurations, although the imaging system 200 has been described as having two detectors 202, 204, in other configurations, the imaging system 200 can include more detectors. For example, similarly to the radiation therapy imaging system 170 the detector 202 can rather be a first imager having multiple detectors (e.g., four detectors), and the detector 204 can be a second imager having multiple detectors (e.g., four detectors). In this case, the sensing area of each of the detectors of the first imager can be smaller than the sensing area of each of the detectors of the second imager. The first imager can be positioned above the second imager so that the second imager is more distally positioned relative to the radiation source than the first imager.

Figure 5:
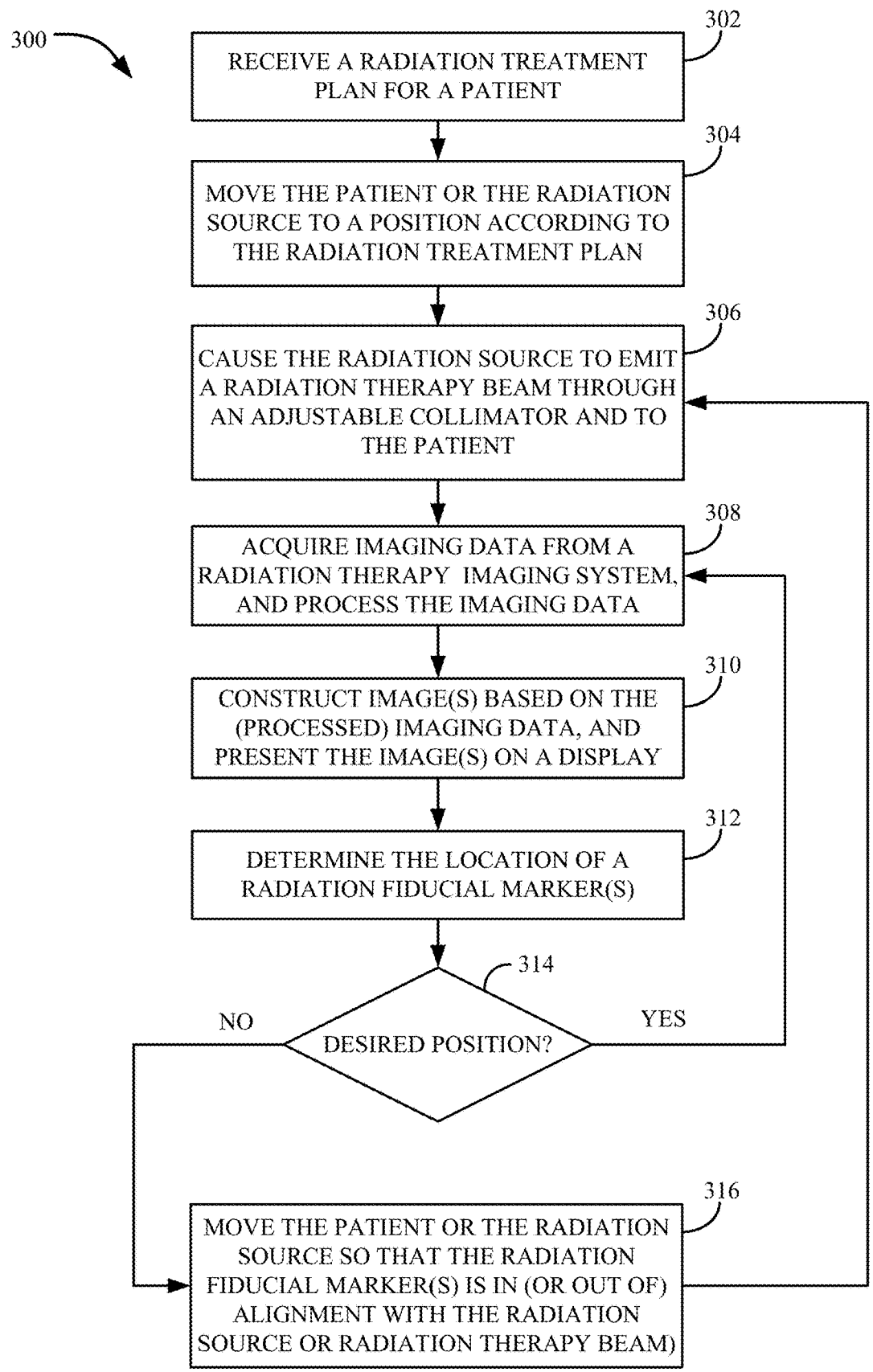
FIG. 5 shows a flowchart of a process for performing a radiation therapy treatment.

FIG. 5 shows a flowchart of a process 300 for performing a radiation therapy treatment, which can be implemented using the radiation therapy system described above. Some or all of the blocks of process 300 can be implemented, as appropriate, using one or more computing devices (e.g., the computing device 112).

At 302, the process 300 can include a computing device receiving a radiation treatment plan for a patient. In some cases, this can include receiving a number of radiation beam paths each having a desired depth, intensity, and duration. In some configurations, this can include preparing the patient for the radiation therapy treatment. For example, a practitioner can couple the one or more radiation fiducial markers to one or more regions of the patient (e.g., implanting the one or more radiation fiducial markers in a tumor, or coupling the radiation fiducial marker to the skin of the patient). As a specific example, this can include implanting one radiation fiducial marker into a tumor of a patient, and coupling a second radiation fiducial marker to the skin surface of the patient so that the second radiation fiducial marker axially intersects with an organ that is not to receive radiation therapy treatment (e.g., the heart). In some configurations, a computing device can receive dimensional data of the regions of the patient, and can relate the locations of the radiation fiducial markers to this dimensional data (e.g., such as if the patient is imaged while placing the radiation fiducial markers).

At 304, the process 300 can include a computing device moving the patient or the radiation source to a position according to the radiation treatment plan. For example, with the patient supported by a table, the computing device can move the table to the position. In other cases, with the patient supported by the table, the computing device can rotate the radiation source to the position.

At 306, the process 300 can include a computing device causing the radiation source to emit a radiation therapy beam through an adjustable collimator and to the patient. As the radiation therapy beam passes through the patient, the radiation therapy beam is provided to the one or more radiation detectors of the radiation therapy imaging system.

At 308, the process 300 can include a computing device acquiring imaging data from a radiation therapy imaging system (e.g., the radiation therapy imaging system 108), an processing the imaging data. In some cases, this can include acquiring imaging data from each radiation detector of the radiation imaging system. In some non-limiting examples, processing the imaging data can include a computing device extracting imaging data corresponding to only the radiation fiducial markers (e.g., spectrally filtering the imaging data).

At 310, the process 300 can include a computing device constructing images based on the imaging data. For example, a computing device can combine imaging data from detectors having similar radiation sensing properties (e.g., imaging data from the detectors 176, 178, 180, 182), which can include adding the imaging data together (e.g., where corresponding acquisition regions of each set of imaging data are added, such as, for example, an upper left region that is spatially the same for each of the detectors 176, 178, 180, 182) an construct an image from the added imaging data. In some non-limiting examples, the images can include a first image constructed from imaging data acquired from one or more radiation detectors tuned to sense a higher levels of radiation. The images can include a second image constructed from imaging data acquire from one or more radiation detectors tuned to sense lower levels of radiation. In other cases, the image can be a combination of the first and second image (e.g., the image 168). In some non-limiting examples, the constructed images can be filtered before or after combining. For example, the computing device can remove fixed pattern noise by filtering an image with a rectangular median filter.

At 310, the process 300 can also include a computing device presenting the one or more images on a display. In some cases, this can include a computing device presenting a combined image on the display that includes, for each radiation fiducial marker, a mark.

At 312, the process 300 can include a computing device determining a location of the radiation fiducial markers, which can include determining a location for each radiation fiducial markers, based on the imaging data. In some non-limiting examples, the computing device can also determine the location of the region of the patient that corresponds to each radiation fiducial marker (e.g., using the dimensional data of the region, and its relationship to the radiation fiducial marker).

At 314, the process 300 can include a computing device determining whether or not each radiation fiducial marker and the corresponding region of the patient (e.g., the tumor) is at a desired position. If at 314, a computing device determines that all the radiation fiducial markers (or the corresponding regions) are at a desired position (or within a positional tolerance), the process 300 can proceed back to block 308 to acquire imaging data from the radiation therapy imaging system. This process can proceed as fast as possible, thus producing a real-time visualization and tracking of the radiation fiducial marker(s).

If at 314, a computing device determines that at least one of the radiation fiducial markers (or their corresponding region) are not at the desired position, or in other words, are outside a positional tolerance, the process can proceed to block 316. For example, if a radiation fiducial marker has been placed in a tumor, and the position of the radiation fiducial marker indicates that the entire tumor is located outside of the higher intensity portion of the radiation therapy beam, based on the imaging data (and in some cases the dimensional data of the tumor), (e.g., outside the portion 120 of the radiation therapy beam 118) the process can proceed to block 316. As another example, if a radiation fiducial marker has been placed on the skin that is over the heart (aligned with an axial axis through the heart), and the position of the radiation fiducial marker indicates that the heart is located within the higher intensity portion of the radiation therapy beam, based on the imaging data (and in some cases the dimensional data of the heart), the process can proceed to block 316.

At 316, the process 300 can include a computing device moving the patient or the radiation source so that the radiation fiducial marker(s) is in (or out of) alignment with the radiation source or the radiation therapy beam. For example, if the radiation fiducial marker is implanted in a tumor of the patient, the computing device can move the radiation therapy beam until the higher intensity portion of the radiation therapy beam is back in alignment with the radiation fiducial marker (and thus the tumor). As another example, if the radiation fiducial marker is coupled to the patient to track the heart, the computing device can move the radiation therapy beam until the higher intensity portion of the radiation therapy beam is out of alignment with the radiation fiducial marker (and thus the tumor). In some cases, before moving the patient or the radiation source, after determining that the radiation fiducial marker is not in a desired position, the computing device can cause the radiation source to stop emitting the radiation therapy beam. In some non-limiting examples, adjusting or stopping the radiation therapy beam after determining that the radiation fiducial markers are not in the desired positions can be advantageous. For example, undesirable irradiation of healthy tissues and non-irradiation of unhealthy tissues (e.g., the tumor) can be decreased, which may improve accuracy and safety of the radiation therapy according to the radiation treatment plan. In some non-limiting examples, after the radiation source or patient has moved, the process 300 can proceed back to block 306. In some cases, the process 300 can proceed until the radiation treatment plan for the patient has finished.

EXAMPLES

The following examples have been presented in order to further illustrate aspects of the disclosure, and are not meant to limit the scope of the disclosure in any way. The examples below are intended to be examples of the present disclosure and these (and other aspects of the disclosure) are not to be bounded by theory.

In radiation therapy, improvements in treatment conformality are often limited by movement of target tissue. To better treat the target, tumor tracking strategies involving beam's-eye-view (BEV) have been explored. However, localization surrogates like implanted fiducial markers may sometimes leave the field-of-view (FOV), as defined by the linear accelerator (LINAC) multi-leaf collimator (MLC). Radiation leakage through the MLC has been measured previously at approximately 1-2%. This discourse explored the possibility of tracking fiducial markers outside the MLC FOV by employing high sensitivity detectors using a high-efficiency, prototype scintillating glass called LKH-5 and also investigated the impact of multi-layer imager (MLI) architecture. It was found that by improving the detector efficiency, using either of these methods, results in a reduction of dose required for fiducial marker visibility. Further, image correction by a rectangular median filter will improve fiducial marker representation in the MLC blocked images. Quantified by measuring the peak-to-sidelobe ratio (PSR) of the normalized cross correlation (NCC) between a template of the fiducial marker with the blocked MLC acquisition, visibility has been found at a threshold of roughly 5 for all configurations with a 3×3 $cm^2$ ROI. For typical gadolinium oxysulfide (GOS) detectors in single and simulated 4-layer configurations, the minimum dose required for visualization was 20 and 10 MU, respectively. For LKH-5 detectors in single and simulated 4-layer configurations, this minimum dose was reduced to 4 and 2 MU, respectively. With a 6 MV flattening filter free (FFF) beam dose rate of 1400 MU/min, the maximum detector frame rate while maintaining fiducial visibility is approximately 12 fps for a 4-layer LKH-5 configuration.

To conduct the experiments, two different EPID panels were studied on the Varian TrueBeam linear accelerator ("LINAC") platform. Both panels were based off the Varian AS-1200 amorphous silicon (aSi) active matrix flat panel imager (AMFPI), featuring 1280×1280 pixels, each 0.336× 0.336 $mm^2$ in pitch. The first EPID was the standard terbium-doped, gadolinium oxysulfide (GOS) panel, commercially available on TrueBeam systems. A 1 mm conversion layer of copper is placed atop 290 µm of powdered GOS phosphor followed by the AS-1200 AMFPI and a lead backing layer. The second EPID differs in that the GOS phosphor is replaced by LKH-5 (Collimated Holes Inc., Campbell, CA), an inexpensive, pixelated scintillating glass. Both copper conversion plate and lead backing layers were removed in the LKH-5 detector. The LKH-5 glass was manufactured at a thickness of 12 mm with 1.51 $mm^2$ square segments. Both the GOS and LKH-5 detectors have been characterized in detail previously.

Figure 6:
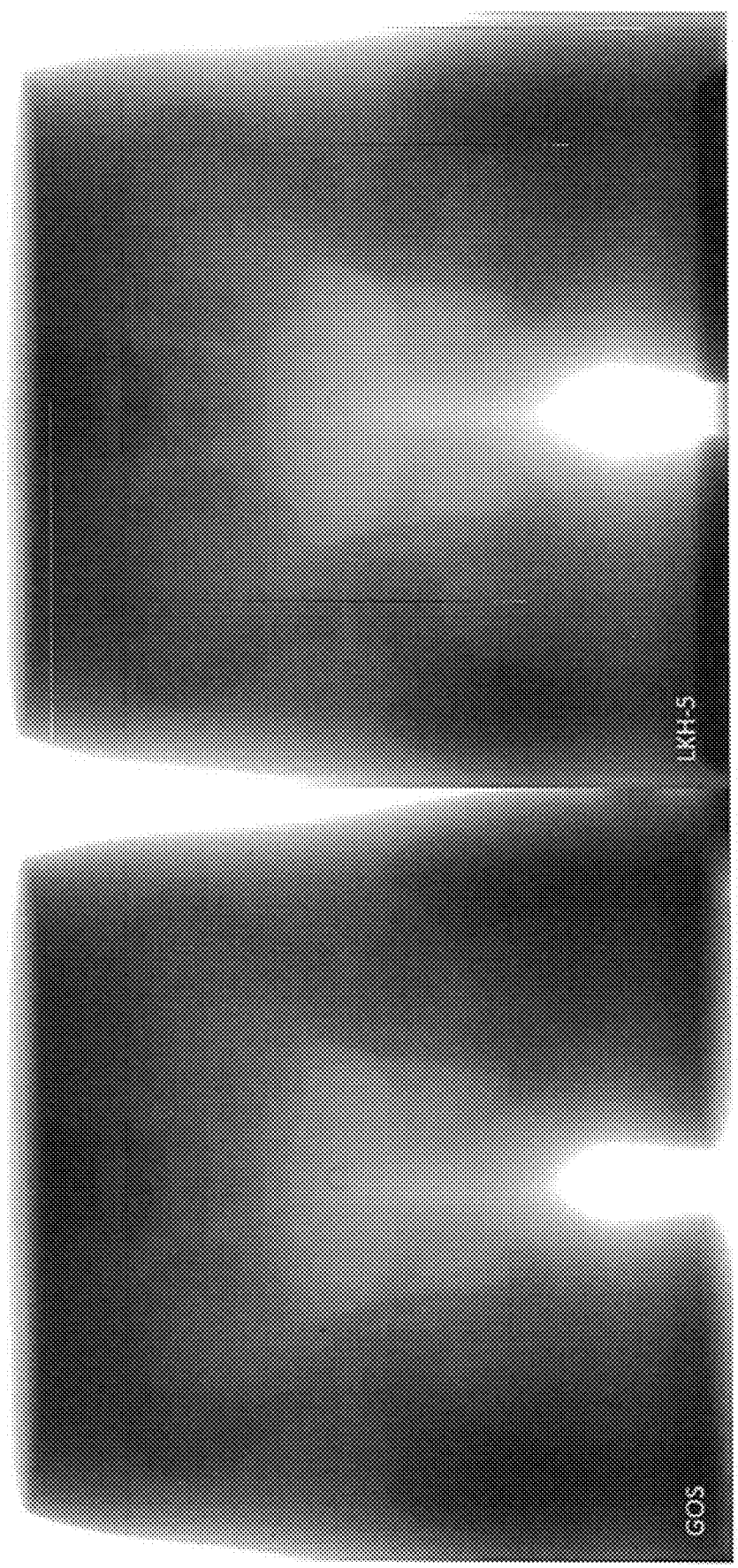
FIG. 6 shows two images of 40×40 cm exposures of the phantom setup using the GOS detector (left) and the LKH-5 detector (right). Both were acquired with a 6×FFF technique at 2 MU and SID=150 cm.

Referring to the images of FIG. 6, a BRAINLAB ET Verification Phantom (The Phantom Laboratory, Greenwich, NY)—an anthropomorphic pelvis phantom—was set up at a source-to-surface distance (SSD) of 100 cm. A 1.15 mm×2 cm, X-MARK gold fiducial marker (ONC Solutions, Acton, MA) was taped to the surface of the pelvis phantom. The phantom was positioned with the fiducial marker at the beam isocenter. The setup was imaged with a 40×40 cm unblocked field at 2 MU as well as an 8×8 jaws-defined field with closed MLC at exposures ranging between 0-50 MU. Studied energies included 6 MV (6×) and 6 MV without applied flattening filter (6×FFF). The imagers under investigation were placed at a source-to-imager distance (SID) of 150 cm.

Closed MLC exposures exhibit greater radiative leakage at the leaf-to-leaf interfaces than behind the center of each leaf, yielding a striping effect on the images. To mitigate this effect and improve the fiducial visibility, a rectangular median filter was applied to the blocked images as described below. The result was subtracted from the original image.

In the photon-starved imaging environment behind the MLC, MLI architecture may provide additional tracking sensitivity due to improved quantum detective efficiency, $\eta$. Since each layer of an MLI may be treated as an independent imager, MLI architecture was simulated by acquiring 4 consecutive frames of the phantom setup and calculating their sum. These measurements were performed for both GOS and LKHS detectors. FIG. 7 shows two phantom images acquired at a beam energy of 6×FFF at doses of 4 MU (left) and 20 MU (right) using the GOS detector. FIG. 8 shows two phantom images acquired at a beam energy of 6×FFF at doses of 4 MU (left) and 20 MU (right) using the LKH-5 detector.

Efficacy of fiducial marker tracking was determined by analyzing the normalized cross correlation (NCC) between a template image and the blocked acquisition. The NCC was calculated using the normxcorr2 function in the MATLAB (MathWorks, Natick MA) image processing toolbox. The template (see FIG. 9) was constructed by acquiring 10 frames of the unblocked image of the phantom setup, and calculating the mean to generate a relatively noise-free representation. A hard threshold was set to define the borders of the fiducial marker and morphological closing was performed to produce a continuous, unbroken object.

The peak-to-sidelobe ratio (PSR) can be used to determine the relative efficacy of tracking based on template matching and the NCC. The PSR was calculated by cropping the NCC map into a 133×133 pixel ROI centered about the fiducial marker location (see FIG. 9), corresponding to an area of approximately 3×3 cm². This ROI represents an area equivalent to the maximum expected lung motion. The peak is defined by the value at the center of the ROI. The sidelobe is defined as the standard deviation of the ROI excluding a circular, sub-ROI with radius=5 pixels, centered about the peak.

To determine an optimal median filter to maximize NCC PSR, median filters ranging from 1-5 pixels wide with lengths of 10-200 pixels were analyzed for a 5 MU blocked acquisition with the LKH-5 detector and a 6 MV beam. The filter dimensions which maximized PSR were determined to be the optimal values. The effect of dose and MLI architecture on NCC PSR was also studied for both GOS and LKH-5 detectors.

FIG. 10 shows a plot of an intensity map of the measured PSR as a function of median filter width and length for a 6×FFF 5 MU blocked acquisition using the LKH-5 detector. The PSR maximizes with a median filter 1 pixel in width and 40 pixels in length.

Examples of 1×40 pixel median filter corrected images may be seen in for 4 MU (left) and 20 MU (right) acquisitions using the GOS (top) and LKH-5 (bottom) detectors. 4 MU and 20 MU represent the minimum doses studied at which the fiducial marker is visible in the LKH-5 and GOS detectors, respectively. The highlighted circle indicates the location of the fiducial marker within the ROI. All images were contrast/leveled to roughly relatively equivalent grayscale.

FIG. 11 shows an intensity map indicating the PSR for several median filter sizes.

FIG. 12 shows two median filter corrected images for 4 MU (left) and 20 MU (right) 6×FFF exposures using the GOS detector. The median filter size was defined as that which produced the maximum PSR in FIG. 12 (1×40 pixels).

FIG. 13 shows two median filter corrected images for 4 MU (left) and 20 MU (right) 6×FFF exposures using the LKH-5 detector. The median filter size was defined as that which produced the maximum PSR in FIG. 12 (1×40 pixels).

FIGS. 14-15 depict 133×133 pixel ROI of the NCC maps for 4 MU and 20 MU acquisitions for each detector. The peaks are located in the center of the plot in all cases. In all but the 4 MU GOS acquisition, a visible peak appears at the center of the ROI.

FIG. 16 shows a scatter plot of the mean PSR as well as the standard deviation over 5 acquisitions as a function of the radiation dose for each of the acquisition energies and detectors. FIG. 17 shows a scatter plot of the standard deviation of the standard deviation (SoS) of the NCC normalized by the mean peak as a function of dose for each of the acquisition energies and detectors. As seen in FIG. 16 the difference in PSR between 6× and 6×FFF is within measured error for both detectors. Further, the LKH-5 detector exhibits a steeper increase in PSR up to approximately 5 MU, above which the value plateaus. The GOS detector exhibits a slower, roughly linear increase over the studied range. The vertical dashed lines indicate the dose threshold at which the fiducial marker is visible on the median filter corrected images, representing a PSR of approximately 5. As indicated by FIG. 17, the SoS, measuring the uncertainty of the sidelobe measurement of the PSR, decreases as a function of dose, with the LKH-5 detector reducing the quantity by a factor of approximately 2.

FIGS. 18-19 shows median filter corrected images (left) as well as NCC maps (right) of simulated 4-layer MLI configurations of the GOS (top) and LKH-5 (bottom) detectors. In both cases the lowest studied dose at which the fiducial marker is visible is presented. For the GOS detector this corresponds to an exposure of 10 MU and for the LKH-5 detector, 2 MU.

FIG. 20 shows a plot of a comparison of PSR for a single layer imager (SLI) configuration (dotted lines) and the simulated MLI configuration (solid lines, 4 layers) of both GOS and LKH-5 based detectors with a beam energy of 6×FFF. The dashed line represents the PSR visibility threshold of 5 as empirically observed in above. In all cases, this threshold of 5 is confirmed over all configurations. For both imagers, the MLI configuration increases PSR over the SLI result. This results in a reduction of the visibility dose threshold.

As shown, the effect of leakage radiation from the MLC interfaces disturbs fiducial marker detection by increasing fixed pattern noise and decreasing effective image dynamic range. The median filter correction results in an equalized appearance. Much of the fixed pattern noise is removed. In all depicted cases, except for 4 MU with the GOS detector, the fiducial marker is visible in the corrected image. Given that the median filter correction was employed to remove the effect of leakage radiation from the MLC, values for the optimal median filter is expected broadly to be general for this particular model of MLC (Varian HD120™) Although there may be some additional observed gains in PSR when performing median filter correction on a patient-by-patient basis, stemming from removal of small scatter and intensity effects inherent with different field sizes and shapes, these effects are expected to be comparatively small.

As shown, increased PSR indicates greater fiducial detectability. For all configurations, a PSR of approximately 5 corresponds to a threshold of qualitative visualization. It should be noted that these PSR thresholds and numerical values are true for the studied 133×133 pixel ROI size, corresponding to an area of 3×3 cm$^2$ at isocenter. A larger ROI size would yield a larger sidelobe, reducing the PSR without affecting the ability to differentiate the peak. Typical patient motion, is not expected to be larger than 2-3 cm. The 133×133 pixel ROI size should be sufficient to track fiducial markers given adequate prior information for most typical clinical cases. For different ROI sizes, thresholds for tracking will necessitate recalibration of PSR thresholds.

For doses below the plateau, as observed for the LKH-5 detector, PSR is roughly linear with dose. Similarly, employing MLI configurations increases photon absorption, reducing image noise and improving PSR. Further, this reduction in noise and improvement in PSR reduces the threshold dose for visualization. The plateau in the LKH-5 detector suggests that past some dose, detection is not limited by stochastic or quantum noise. Further reduction of noise by increasing dose will not improve NCC performance. This feature may be the result of a combination of the relatively low resolution of the LKH-5 detector resulting in inadequate reproduction of phase information. Given the relatively large size of the scintillation segments of the LKH-5 detector (1.51×1.51 mm$^2$) subtle image shifts, either caused by motion or relative location of MLCs with respect to the detector, may cause reductions in both absolute and maximum NCC. Further study of the plateau region is the subject of further investigation. Employing MLI architecture increases the value of this plateau. The GOS detector, with relatively poorer PSR performance and improved imager resolution does not exhibit an imaging plateau at the studied range of doses. While little difference is observed between 6× and 6×FFF beam energies for either detector, harder and higher energy beams should generally result in greater quantities of leakage radiation, resulting in improved PSR or detectability. 6× and 6×FFF beams may not be sufficiently differentiated after passage through the MLC to yield a noticeable difference in PSR result.

For the SLI and MLI LKH-5 imagers, the threshold of visibility is roughly 4 MU and 2 MU, respectively. For the MLI GOS imager, this threshold is approximately 10 MU. For a 6×FFF treatment with a dose-rate of 1400 MU/min, this corresponds to an imager framerate of 5.8 FPS and 11.7 FPS for the SLI and MLI LKH-5 detectors, respectively, and 2.3 FPS for the MLI GOS imager. Framerates greater than 4.29 FPS have been shown to be sufficient for in-treatment BEV tumor tracking without fiducial markers.

Although the template is an unblocked acquisition of an identical setup to the blocked acquisitions, the trends, while perhaps with lower absolute PSR values, should be consistent with other template types. In real, practical situations such as VMAT treatment, similar template data may be acquired by forward projecting planning CT images to the predicted angles of acquisition during treatment. Given an ROI of 3×3 cm$^2$ at isocenter should allow for a large degree of patient motion given prior knowledge. As shown, NCC PSR, allows for inter-modality templates as well as some deviation in terms of rotation and translation between simulation and treatment. Although the present study analyzes NCC PSR in context of simple shifts of the template as compared to the acquired blocked images, clinically, rotations may reduce these values. However, this effect is not unique to blocked tracking specifically and has been the topic of study previously.

To enable fiducial tracking throughout radiotherapy delivery, within the aperture as well as behind the MLC, we propose a high-dynamic range (HDR) design. The concept uses two imager layers (having a number of detectors), one to image within the opening of the MLC aperture (e.g., using GOS) and one to image outside of the aperture (e.g., using LKH-5). By combining the information from each layer and strategically masking out regions of high saturation for the second imager, all fiducial markers will be potentially available for tumor tracking over all imaging control points. This will improve the fidelity of the measurement while also allowing treatment planning to proceed without special consideration to marker locations. Further investigation of such a device is ongoing and will be the subject of future work.

Some aspects of the disclosure provide an improvement for fiducial marker visibility behind closed MLC leaves, which may enable real-time tumor tracking without the need for kV imaging, surface surrogates, or re-planning to ensure fiducial visibility at control points. The feasibility of in-treatment BEV tumor tracking of fiducial markers behind closed MLC leaves was confirmed using high-sensitivity, highly efficient MV detectors. Generally, increasing sensitivity and reducing quantum noise, by improved scintillation materials and MLI architecture, improves fiducial trackability. Visibility thresholds were consistent across detector configurations and scintillation materials with sufficiently large FOV at relevant treatment dosages and framerates.

The present disclosure has described one or more preferred non-limiting examples, and it should be appreciated that many equivalents, alternatives, variations, and modifications, aside from those expressly stated, are possible and within the scope of the invention.

It is to be understood that the disclosure is not limited in its application to the details of construction and the arrangement of components set forth in the following description or illustrated in the following drawings. The disclosure is capable of other non-limiting examples and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, unless otherwise limited or defined, discussion of particular directions is provided by example only, with regard to particular non-limiting examples or relevant illustrations. For example, discussion of "top," "front," or "back" features is generally intended as a description only of the orientation of such features relative to a reference frame of a particular example or illustration. Correspondingly, for example, a "top" feature may sometimes be disposed below a "bottom" feature (and so on), in some arrangements or non-limiting examples. Further, references to particular rotational or other movements (e.g., counterclockwise rotation) is generally intended as a description only of movement relative a reference frame of a particular example of illustration.

In some non-limiting examples, aspects of the disclosure, including computerized implementations of methods according to the disclosure, can be implemented as a system, method, apparatus, or article of manufacture using standard programming or engineering techniques to produce software, firmware, hardware, or any combination thereof to control a processor device (e.g., a serial or parallel general purpose or specialized processor chip, a single- or multi-core chip, a microprocessor, a field programmable gate array, any variety of combinations of a control unit, arithmetic logic unit, and processor register, and so on), a computer (e.g., a processor device operatively coupled to a memory), or another electronically operated controller to implement aspects detailed herein. Accordingly, for example, non-limiting examples of the disclosure can be implemented as a set of instructions, tangibly embodied on a non-transitory computer-readable media, such that a processor device can implement the instructions based upon reading the instructions from the computer-readable media. Some non-limiting examples of the disclosure can include (or utilize) a control device such as an automation device, a special purpose or general purpose computer including various computer hardware, software, firmware, and so on, consistent with the discussion below. As specific examples, a control device can include a processor, a microcontroller, a field-programmable gate array, a programmable logic controller, logic gates etc., and other typical components that are known in the art for implementation of appropriate functionality (e.g., memory, communication systems, power sources, user interfaces and other inputs, etc.).

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally it should be appreciated that a carrier wave can be employed to carry computer-readable electronic data such as those used in transmitting and receiving electronic mail or in accessing a network such as the Internet or a local area network (LAN). Those skilled in the art will recognize that many modifications may be made to these configurations without departing from the scope or spirit of the claimed subject matter.

Certain operations of methods according to the disclosure, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular non-limiting examples of the disclosure. Further, in some non-limiting examples, certain operations can be executed in parallel, including by dedicated parallel processing devices, or separate computing devices configured to interoperate as part of a large system.

As used herein in the context of computer implementation, unless otherwise specified or limited, the terms "component," "system," "module," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as non-limiting examples of the disclosure, of the utilized features and implemented capabilities of such device or system.

As used herein, unless otherwise defined or limited, ordinal numbers are used herein for convenience of reference based generally on the order in which particular components are presented for the relevant part of the disclosure. In this regard, for example, designations such as "first," "second," etc., generally indicate only the order in which the relevant component is introduced for discussion and generally do not indicate or require a particular spatial arrangement, functional or structural primacy or order.

As used herein, unless otherwise defined or limited, directional terms are used for convenience of reference for discussion of particular figures or examples. For example, references to downward (or other) directions or top (or other) positions may be used to discuss aspects of a particular example or figure, but do not necessarily require similar orientation or geometry in all installations or configurations.

This discussion is presented to enable a person skilled in the art to make and use non-limiting examples of the disclosure. Various modifications to the illustrated examples will be readily apparent to those skilled in the art, and the generic principles herein can be applied to other examples and applications without departing from the principles disclosed herein. Thus, non-limiting examples of the disclosure are not intended to be limited to non-limiting examples shown, but are to be accorded the widest scope consistent with the principles and features disclosed herein and the claims below. The following detailed description is to be read with reference to the figures, in which like elements in different figures have like reference numerals. The figures, which are not necessarily to scale, depict selected examples and are not intended to limit the scope of the disclosure. Skilled artisans will recognize the examples provided herein have many useful alternatives and fall within the scope of the disclosure.

Various features and advantages of the disclosure are set forth in the following claims.

The invention claimed is:

1. A radiation therapy system comprising:
a radiation source configured to emit a radiation therapy beam;
a collimator positioned to attenuate at least a periphery of the radiation therapy beam;
a radiation fiducial configured to be coupled to a patient;
a first radiation detector having a first plurality of sensing elements each configured to sense radiation that interacts with the respective sensing element;
a second radiation detector having a second plurality of sensing elements each configured to sense radiation that interacts with the respective sensing element, wherein the second radiation detector is arranged more distally from the radiation source than the first radiation detector to receive the radiation therapy beam after the first radiation detector;
a computing device in communication with the radiation source, the first radiation detector, and the second radiation detector, the computing device being configured to:
receive first imaging data from the first radiation detector;
receive second imaging data from the second radiation detector; and
track a position of the imaging fiducial within or outside the attenuated periphery of the radiation therapy beam using the first imaging data and the second imaging data.

2. The radiation therapy system of claim 1, wherein the first radiation detector has a first gain, and the second radiation detector has a second gain, and wherein the second gain of the second radiation detector is greater than the first gain of the first radiation detector.

3. The radiation therapy system of claim 2, wherein the first radiation detector includes a gadolinium oxysulfide (GOS) detector, and
wherein the second radiation detector includes a layer of a LKH-5 scintillating glass.

4. The radiation therapy system of claim 1, wherein the computing device is configured to:
generate a first image using the first imaging data;
generate a second image using the second imaging data; and
combine the first image and the second image by weighting the second image over the first image when the fiducial is within the periphery of the radiation therapy beam.

5. The radiation therapy system of claim 4, wherein the computing device is configured to:

segment a portion of the second image that corresponds to an envelope of the periphery of the radiation therapy beam; and
locate the imaging fiducial in a remaining portion of the second image that does not include the envelope of the periphery of the radiation therapy beam, to determine that the fiducial is within the periphery of the radiation therapy beam.

6. The radiation therapy system of claim 5, wherein the computing device is further configured to process the remaining portion of the second image by filtering the remaining portion of the second image using a median filter having a width and a length, and
wherein a ratio of the length to the width of the median filter is approximately 40.

7. The radiation therapy system of claim 5, wherein the remaining portion of the second image surrounds and encapsulates the envelope of the periphery of the radiation therapy beam to define a circular void.

8. The radiation therapy system of claim 5, wherein at least one of:
the region defined by the portion of the second image that corresponds to the envelope is a predefined region, the size and shape of the predefined region being based on the properties of the radiation beam and a distance the radiation beam traverses along a path from the collimator and to the first radiation detector; or
the computing device is configured to determine a boundary of the envelope of the periphery of the radiation therapy beam from the first image, the boundary of the envelope of the periphery being used to define the portion of the second image that is to be segmented.

9. The radiation therapy system of claim 4, wherein, to combine the first image and the second image, the computing device is configured to:
subtract the second image from the first image to generate a subtracted second image; and
locate the imaging fiducial in the subtracted second image.

10. The radiation therapy system of claim 1, wherein the first plurality of sensing elements defines a first sensing area of the first radiation detector,
wherein the second plurality of sensing elements defines a second sensing area of the second radiation detector, and
wherein the first sensing area is substantially aligned with the second sensing area so that the first sensing area substantially overlaps with the second sensing area.

11. The radiation therapy system of claim 10, wherein at least one of:
the first sensing area is substantially similar to the second sensing area;
the size of each of the first plurality of sensing elements is substantially similar to the size of each of the second plurality of sensing elements, or
the number of the first plurality of sensing elements is substantially similar to the number of the second plurality of sensing elements.

12. The radiation therapy system of claim 1, further comprising:
a third radiation detector having a third plurality of sensing elements each configured to sense radiation that interacts with the respective sensing element; and
a fourth radiation detector having a fourth plurality of sensing elements each configured to sense radiation that interacts with the respective sensing element; and wherein the second radiation detector is situated more proximate to the radiation source than the third radiation detector, and the third radiation detector is situated more proximate to the radiation source than the fourth radiation detector, and wherein the computing device is configured to:
receive third imaging data from the third radiation detector;
receive fourth imaging data from the fourth radiation detector;
generate a first image from the first imaging data;
generate a second image by combining at least two of the second imaging data, the third imaging data, or the fourth imaging data; and
locate the imaging fiducial in the second image to track the position of the imaging fiducial.

13. The radiation therapy system of claim 12, wherein generating the second image includes the computing device being configured to:
combine the second imaging data, the third imaging data, and the fourth imaging data together to generate combined imaging data; and
generate the second image using the combined imaging data, and
wherein the computing device is configured to:
at least one of segment a portion of the second image that corresponds to a region within the attenuated periphery of the radiation therapy beam, or subtract the second image from the first image to generate a subtracted second image; and
locate the imaging fiducial in the remaining portion of the second image, or the subtracted second image.

14. The radiation therapy system of claim 12, wherein gains of the second, third, and fourth detectors are substantially similar, and
wherein a gain of the second detector is greater than a gain of the first detector.

15. The radiation therapy system of claim 1, wherein the first imaging data is first three-dimensional (3D) imaging data, and
wherein the second imaging data is second 3D imaging data.

16. A method for performing a radiation therapy treatment comprising:
delivering a radiation therapy beam from a radiation source to a patient having a fiducial marker positioned on the patient during a radiation therapy treatment;
receiving the radiation therapy beam after passing through the patient using a first radiation detector tuned to acquire first imaging data;
attenuating at least a portion of the radiation therapy beam as it travels from the radiation source to the patient;
receiving the radiation therapy beam after passing through the patient using a second radiation detector tuned to acquire second imaging data at an attenuated intensity level corresponding to the portion of the radiation therapy beam that is attenuated;
receiving, using one or more processors, the first imaging data and the second imaging data;
reconstructing, using the one or more processors, images including the fiducial marker based on the first and second imaging data, when the fiducial marker is irradiated by the at least a portion of the radiation therapy beam that is attenuated;
generating, a first image using the first imaging data and a second image using the second imaging data;

combing the first image and the second image by weighting the second image over the first image when the fiducial is within the periphery of the radiation therapy beam;
subtracting the second image from the first image to generate a subtracted second image; and
locating the imaging fiducial in the subtracted second image.

17. The method of claim 16, wherein the gain of the second radiation detector is greater than the gain of the first radiation detector.

18. The method of claim 16, further comprising combining the first and second imaging data to track a position of the fiducial marker.

19. A radiation therapy system comprising:
a radiation source configured to emit a radiation therapy beam toward a patient at a selected energy level;
a collimator positioned to receive the radiation therapy beam before reaching the patient and to attenuate at least a periphery of the radiation therapy beam to an attenuated intensity level;
a radiation fiducial configured to be coupled to a patient;
a first radiation detector positioned to acquire first imaging data from the patient using a first plurality of sensing elements tuned to acquire the radiation therapy beam at the selected intensity level;
a second radiation detector positioned to acquire second imaging data from the patient using a second plurality of sensing elements tuned to acquire the radiation therapy beam at the attenuated intensity level;
a processor configured to receive the first imaging data and the second imaging data and selective combine the first imaging data and the second imaging data to track the position of the imaging fiducial in an attenuated periphery of the radiation therapy beam.

20. The radiation therapy system of claim 19, wherein the gain of the second radiation detector is greater than the gain of the first radiation detector.

21. The radiation therapy system of claim 19, wherein the processor is configured to generate a first image using the first imaging data and a second image using the second imaging data and combine the first image and the second image by weighting the second image over the first image when the fiducial is within the periphery of the radiation therapy beam; and
the processor configured to subtract the second image from the first image to generate a subtracted second image and locate the imaging fiducial in the subtracted second image.

22. The radiation therapy system of claim 21, wherein the processor is configured to:
segment a portion of the second image that corresponds to an envelope of the periphery of the radiation therapy beam; and
locate the imaging fiducial in a remaining portion of the second image that does not include the envelope of the periphery of the radiation therapy beam, to determine that the fiducial is within the periphery of the radiation therapy beam.

23. The radiation therapy system of claim 22, wherein the remaining portion of the second image surrounds and encapsulates the envelope of the periphery of the radiation therapy beam to define a circular void.

24. The radiation therapy system of claim 21, wherein the first plurality of sensing elements defines a first sensing area of the first radiation detector, wherein the second plurality of sensing elements defines a second sensing area of the second radiation detector, and wherein the first sensing area is substantially aligned with the second sensing area so that the first sensing area substantially overlaps with the second sensing area.

\* \* \* \* \*

UNITED STATES PATENT AND TRADEMARK OFFICE
CERTIFICATE OF CORRECTION

PATENT NO. : 11,998,762 B2
APPLICATION NO. : 17/114077
DATED : June 4, 2024
INVENTOR(S) : Ross Berbeco et al.

Page 1 of 1

It is certified that error appears in the above-identified patent and that said Letters Patent is hereby corrected as shown below:

In the Specification

Column 25, Line 30, "LKHS" should be --LKH5--.

Signed and Sealed this
Twenty-fourth Day of September, 2024

Katherine Kelly Vidal
*Director of the United States Patent and Trademark Office*